(12) United States Patent
Van Sleeuwen et al.

(10) Patent No.: US 12,379,774 B2
(45) Date of Patent: Aug. 5, 2025

(54) USER GESTURE DATA COLLECTION SYSTEM, MULTISENSORY EXPERIENCE SYSTEM AND CORRESPONDING METHODS

(71) Applicant: Firmenich SA, Satigny (CH)

(72) Inventors: Rutger M. T. Van Sleeuwen, Plainsboro, NJ (US); Leo Feng, Plainsboro, NJ (US); Amy Gonzalez, Plainsboro, NJ (US)

(*) Notice: Subject to any disclaimer, the term of this patent is extended or adjusted under 35 U.S.C. 154(b) by 0 days.

(21) Appl. No.: 17/794,805

(22) PCT Filed: Jan. 22, 2021

(86) PCT No.: PCT/EP2021/051533
§ 371 (c)(1),
(2) Date: Jul. 22, 2022

(87) PCT Pub. No.: WO2021/148659
PCT Pub. Date: Jul. 29, 2021

(65) Prior Publication Data
US 2023/0146448 A1 May 11, 2023

Related U.S. Application Data

(60) Provisional application No. 62/965,285, filed on Jan. 24, 2020, provisional application No. 62/965,277, filed on Jan. 24, 2020.

(30) Foreign Application Priority Data

Mar. 18, 2020 (EP) .................................. 20163997
Mar. 19, 2020 (EP) .................................. 20164323

(51) Int. Cl.
*G06F 3/01* (2006.01)
*A61L 9/03* (2006.01)

(52) U.S. Cl.
CPC .............. *G06F 3/012* (2013.01); *A61L 9/035* (2013.01); *G06F 3/017* (2013.01); *A61L 2209/111* (2013.01)

(58) Field of Classification Search
CPC . G06F 3/012; G06F 3/017; G06F 3/01; A61L 9/035; A61L 2209/111; A61L 9/14
See application file for complete search history.

(56) References Cited

U.S. PATENT DOCUMENTS 4,934,386 A * 6/1990 Walker .................... A61B 5/087
434/236
2004/0204043 A1* 10/2004 Wang ...................... H04M 1/21
455/575.1

(Continued)

FOREIGN PATENT DOCUMENTS

CN      208 920 486 U     5/2019
WO      WO 2017/077364 A1 * 5/2017

OTHER PUBLICATIONS

Narumi et al, "Pseudo-gustatory display system based on cross-modal integration of vision, olfaction and gustation", IEEE 2011 Virtual Reality Conference (VR), pp. 127-130, (2011).

*Primary Examiner* — Md Saiful A Siddiqui
(74) *Attorney, Agent, or Firm* — PatShegen IP; Moshe Pinchas

(57) ABSTRACT

The user gesture data collection system (100), comprises: —a portable (105) fragrance delivery device, —a relative positioning tracker (110) configured to detect the positioning of the portable fragrance device relative a facial feature of a user and —a data storing means (115) storing data based on the relative positioning detected.

29 Claims, 14 Drawing Sheets

(56) References Cited

U.S. PATENT DOCUMENTS

| | | | |
|---|---|---|---|
| 2010/0309434 A1* | 12/2010 | Van Schijndel | A61L 9/125 |
| | | | 352/85 |
| 2011/0130877 A1* | 6/2011 | Lynch | A61L 9/14 |
| | | | 239/34 |
| 2016/0379506 A1* | 12/2016 | Okada | G09B 19/00 |
| | | | 434/236 |
| 2017/0224085 A1* | 8/2017 | Dupont | A45D 40/0087 |
| 2018/0071425 A1* | 3/2018 | Jin | A61L 9/14 |
| 2018/0286351 A1 | 10/2018 | Fateh | |
| 2018/0357647 A1* | 12/2018 | Ur | A63J 25/00 |
| 2018/0369847 A1* | 12/2018 | Kihm | A61L 9/14 |
| 2018/0373272 A1* | 12/2018 | Kihm | B64D 1/18 |
| 2020/0289694 A1* | 9/2020 | Kelsen | A61L 9/122 |
| 2021/0077374 A1* | 3/2021 | Prigge | A61K 8/35 |
| 2021/0187148 A1* | 6/2021 | Sivagaminathan | G07F 17/18 |

\* cited by examiner

USER GESTURE DATA COLLECTION SYSTEM, MULTISENSORY EXPERIENCE SYSTEM AND CORRESPONDING METHODS

This present application is a U.S. national phase entry under 35 U.S.C. § 371 of PCT Application No. PCT/EP2021/051533, filed Jan. 22, 2021, which claims priority to U.S. Application Ser. No. 62/965,277, filed Jan. 24, 2020, and U.S. Application Ser. No. 62/965,285, filed Jan. 24, 2020, as well as European Patent Application No. 20163997.8, filed Mar. 18, 2020, and European Patent Application No. 20164323.6, filed Mar. 19, 2020. The entire contents of these applications are explicitly incorporated herein by this reference.

TECHNICAL FIELD OF THE INVENTION

The present invention relates to a user gesture data collection system, to a multisensory experience system and the corresponding methods. It applies, for example, to the field of human behavior monitoring relative to fragrances, such as fragrances used in fine fragrance, personal care, laundry care or home care.

BACKGROUND OF THE INVENTION

In the field of fragrance design, particularly of perfumery and flavor design, key quantitative and qualitative metrics are observed to determine whether a designed fragrance is performing as intended by its creator. These metrics rely on the physicochemical, psychophysical and sensorial properties of the fragrance.

The quantitative and qualitative metrics are measured or observed based on available data, whether obtained by automatic sensors or reported by panelists based on their own personal perceptions. This data, in turn, allows fragrance designers to model the likely perception of users, and design fragrance accordingly, or to receive feedback on their creations in a trial and error scenario.

Current data and models, however, fail to consider and monitor the behavior of subjects exposed to fragrances. Such limitation, in turn, means that less knowledge is available for fragrance designers.

Newer subject interaction monitoring systems use technologies such as augmented reality (AR), virtual reality (VR) or mixed reality (MR) systems to provide augmented sensorial inputs to subjects by combining such systems with fragrance delivery devices.

However, such systems only focus on the virtual interaction of the subject with fragrances, providing little to no useful information for fragrance designers aiming to know more about real-life fragrance-subject interactions.

Currently, no satisfying systems exists that would monitor, with high fidelity, the behavior of a subject in relation to a fragrance.

Furthermore, such systems typically use active fragrance delivery systems, using pumps, fans or dispensers, to create an airflow pushing the fragrance towards the user. Such systems present many problems:

the fragrance is imposed on the user—the user cannot easily escape from the fragrance other than pulling the headset off, which disturbs the experience; this can also cause discomfort which is likely to be counterproductive for health and wellbeing applications, the fragrance is delivered with a delay since the fragrance has to be actuated, or released—the fragrance delivery lacks fidelity since it is nearly impossible to present the fragrance to the user with the right delay, the right dilution or concentration that would be observed if they interacted with an actual fragranced article of interest, the behavior of the user is unnatural with regards to real-life interaction with fragrant sources, these systems fail to reveal the interaction between a fragrance and its base or substrate, since the character of a fragrance may change if it is presented as a fragrance oil or mixed in a laundry detergent for example and it is hard in these systems to present a user with an unfragranced control; for example just smelling a laundry detergent base can be beneficial before smelling fragranced versions.

US Patent Application US2018/071425 discloses different devices to passively deliver a fragrance directly into the nostrils of a user.

Chinese Utility model CN2082086 discloses an air conditioning unit capable of adjusting airflow to augmented reality information.

Furthermore, the article "*Pseudo-gustatory display system based on cross-modal integration of vison, olfaction and gustation*" by Takuji Narumi et al. and US Patent Application US 2018/286351 disclose related prior art.

In US Patent application US2018/0369847, a mobile fragrance discharge device is disclosed. Two embodiments are shown, a cleaning robot and a fragrance drone. The cleaning robot is independent of the user. The fragrance drone comprises an active discharge device. In other terms, the fragrance is projected out of the device. This type of discharge device modifies the behavior of a subject in relation to a fragrance as it is brought to the subject.

Currently, no satisfying systems exists that would monitor, with high fidelity, the gestural behavior of a human subject in relation to a fragrance.

SUMMARY OF THE INVENTION

The present invention is intended to remedy all or part of these disadvantages.

To this effect, according to a first aspect, the present invention aims at a user gesture data collection system, comprising:

a portable fragrance delivery device, a relative positioning tracker configured to detect the positioning of the portable fragrance device relative a facial feature of a user and a data storing means storing data based on the relative positioning detected.

Thanks to these provisions, a user's physical behavior relative to a fragrance that can be held and moved around by said user can be monitored. Such interaction monitoring provides valuable modelling opportunities to detect, for example, how much a user appreciates a fragrance or to quantify the strength of a fragrance based on the distance at which is kept the portable device from the face of the user. The collected data can thus be used to determine fragrance performance indicators.

As the fragrance device is tracked, preferably in a three dimensional referential, allowing the user to bring the fragranced article to one's nose to evaluate the character, intensity and other quality attributes of a fragrance with great fidelity, while data is collected on a user's gestures during the experience.

In particular embodiments, the user gesture data collection system further comprises a virtual spatial fragrance zone modeling means configured to define a virtual volume in proximity of the fragrance delivery device, the relative positioning tracker being configured to detect the positioning of the virtual spatial fragrance zone relative to the tracked facial feature.

Such embodiments allow for more precise interaction data collection as the fragrance detection zone is modelled, this in turn allows greater precision than the monitoring of the interactions of the user with the device as such.

In particular embodiments, the user gesture data collection system further comprises a virtual user smelling zone modeling means configured to define a virtual volume in proximity of the tracked facial feature, the relative positioning tracker being configured to detect the positioning of the portable fragrance device or the virtual spatial fragrance zone relative to the virtual user smelling zone.

Such embodiments allow for more precise interaction data collection as the fragrance detection zone of the user, that is the zone around the nose, is modelled. This in turn allows greater precision than the monitoring of the interactions of the user's face as such.

In particular embodiments, the user gesture data collection system further comprises a user breathing cycle modeling means, the user smelling zone being defined as a function of the modelled breathing cycle.

Such embodiments allow for the definition of a dynamic smelling zone corresponding to the effective breathing of the operator of the system.

In particular embodiments, the user gesture data collection system further comprises:
  a digital environment display configured to be worn on the head of the user,
  a spatial position tracking means being configured to track the position of the digital environment display,
  a facial position inference means configured to infer the position of the facial feature based on the digital environment display position tracked.

Such embodiments allow providing visual and audio sensorial input to the user and monitoring the interactions of the user with combined sensorial inputs including more than the fragrance itself. Furthermore, the positioning and/or tracking of the display on the head of the user can be used as a proxy to any part of the face of the user, which is known by the system to be in the vicinity of the display.

In particular embodiments, the portable fragrance delivery device comprises a fragrance selector configured to present at least one determined fragrance among a plurality of fragrances.

Such embodiments allow to monitor the interactions of a user in response to each fragrance presented.

In particular embodiments, the user gesture data collection system further comprises a digital environment event detector, the selector being actuated as a function of the digital event detected.

Such embodiments allow the matching of visual and/or audio stimuli with a given fragrance associated to said stimuli.

In particular embodiments, the portable fragrance delivery device comprises a passive fragrance delivery means.

Such embodiments do not impose a fragrance on the user; the user chooses how strongly, how often or close the fragrance is perceived. This is especially relevant for wellbeing and health where the fragrance experience can be personalized. Systems that have fragrance release devices mounted below the nose suffer from the limitation that the user cannot easily escape from the fragrance other than pulling the headset off, which disturbs the experience. This can also cause discomfort which is likely to be counterproductive for health and wellbeing applications. If a user senses an unpleasant fragrance using the system object of the present invention, the user can simply move his or her hand/arm or head away moving the fragrance zone and smelling zone away from another.

Such embodiments have no delay, since the fragrance does not have to be actuated, or released. In these embodiments, the fragrance is presented passively, in in a manner that reflects a "real-world" fragranced article represented by the delivery device and associated fragrance(s).

Such embodiments have the ability to present the user with an unfragranced control (e.g. a blotter, a reed, an unscented towel without fragrance). This is critical in consumer evaluation studies.

Such embodiments represent the way that perfumers/creators/consumers already interact with fragrance and fragranced articles on a daily basis: i.e. passively without actuating, spraying, the use of fans, heaters (heaters would only be used in case this represents a real-life scenario. For example, having a heater to gently warm up artificial skin to approximately 32° C. would be a good way to further improve the fidelity of a fragrance evaluation on skin).

Such embodiments are very suitable for users to rate the fragrance experienced using a star or point rating (e.g. 1-5 stars, rating 1-10).

Such embodiments are for people to show purchase intent or for e-commerce purposes.

Such embodiments allow for greater fragrance fidelity, allowing for higher fidelity user interaction monitoring.

In particular embodiments, the user gesture data collection system further comprises a robotic arm configured to hold the portable fragrance delivery device.

Such embodiments allow for a more controlled monitoring to take place, limiting the gestures of the users with respect to the delivery device.

In particular embodiments, the portable fragrance delivery device comprises an artificial human body part (e.g. artificial skin) or a fragranced item representation upon which the fragrance is applied.

Such embodiments allow for greater fragrance fidelity, allowing for higher fidelity user interaction monitoring.

In particular embodiments, the user gesture data collection system further comprises a user gesture detection means, the data stored corresponding at least in part to the detected user gesture.

Such embodiments allow not only to store positioning data, but also allow to store user gesture representative data. The determination of said gestures depends on the type of gesture to monitor.

In particular embodiments, the user gesture detection means is configured to detect a gesture corresponding to a smelling event by the user, such event being detected as a function of the relative distance between the facial feature and the portable fragrance device. In more advanced embodiments, the smelling event is detected by a collision between fragrance zone and smelling zone.

In particular embodiments, the user gesture data collection system further comprises a relative position evolution measurement means configured to determine, over time, the position of the portable fragrance delivery device relative to the position of the facial feature, the user gesture detection means being configured to detect a user gesture based on the relative position evolution measured.

Such embodiments allow for the determination of gestures based not only on relative positioning, but on the evolution of that positioning over time.

In particular embodiments, the user gesture data collection system further comprises a user body behavior detection means, or an ambient physical parameter sensor, such body behavior or an ambient physical parameter being stored by the storing means.

Such embodiments allow for the monitoring of further user or environment parameters.

In particular embodiments, the user gesture data collection system further comprises a fragrance physical parameter detection means, the fragrance physical parameter detected being stored by the storing means.

Such embodiments allow for the comparison of user interaction monitoring versus data collected by the physical parameter detection means.

In particular embodiments, the user gesture data collection system further comprises a user input means, said user input being stored by the storing means.

Such embodiments allow for the comparison or association of explicit user input versus implicit user input, in this case the stored gesture data.

In particular embodiments, the user gesture data collection system further comprises at least one other non-verbal physiological measuring device. Such a non-verbal physiological measuring device can be pulse monitoring devices of brain activity mapping, in particular EEG (Electroencephalogram). By combining additional non-verbal measurement devices, the system can result in novel quantifiable parameters, which enable perfumers to design, in an objective manner, performant and sophisticated perfume compositions that positively impact mood and emotions or impart sensorial benefits.

In particular embodiments, the user gesture data collection system further comprises a fragrance spatial mass transfer calculation means and an itinerary definition means configured to determine a route to be followed by an operator as a function of the spatial mass transfer calculated, the relative position tracker being configured to operate in different locations of the route defined.

Such embodiments allow for the determination of the volume of fragranced air surrounding a fragrance source. Such information allows for much more accurate user-behavior observations. Furthermore, the definition of an itinerary to be followed, based upon the volume and/or concentration of fragranced air determined, allows for the evaluation by the user of the fragrance at different preset locations corresponding to specific predetermined experimental locations and/or fragranced air concentration. For example, such measurements can be set at the boundary of the determined volume, halfway from the boundary to the source and in the near vicinity of the source.

In particular embodiments, In particular embodiments, the user gesture data collection system further comprises a fragrance spatial mass transfer calculation means without an itinerary definition means configured to determine a route to be followed by an operator as a function of the spatial mass transfer calculated, the relative position tracker being configured to operate in different locations of the route defined.

Such simplified embodiments allow for the information relative to the volume of fragranced air within the rest of the system without considering the need for itineraries and routes.

In particular embodiments, the user gesture data collection system further comprises a portable fragrance delivery device activation detection means, the relative positioning tracker being activated as a function of said detected activation.

Such embodiments allow for the use of the system with active fragrance delivery devices, in which the activation of the delivery device can thus be monitored and taken in consideration when observation the collected data. Such activation can correspond to a timestamp of initial fragrance release.

According to a second aspect, the present invention aims at a user gesture data collection method, comprising:
- a fragrance delivery step operated by a portable fragrance delivery device,
- a relative positioning tracking step to detect the positioning of the portable fragrance device relative a facial feature of a user and
- a data storing step storing data based on the relative positioning detected.

The advantages of said method correspond to the respective system.

According to a third aspect, the present invention aims at a multisensory experience system, comprising:
- a user gesture data collection system, object of the present invention, comprising:
  - a passive and portable fragrance delivery device,
  - a delivery device position tracking means,
  - a delivery device position converter configured to convert the tracked position of the device into a virtual environment position and
- a digital environment display comprising a modeling means configured to model, in the digital environment, a virtual image in a position corresponding to the tracked delivery device.

Such provisions do not impose a fragrance on the user; the user chooses how strongly, how often or close the fragrance is perceived. This is especially relevant for wellbeing and health where the fragrance experience can be personalized. Systems that have fragrance release devices mounted below the nose suffer from the limitation that the user cannot easily escape from the fragrance other than pulling the headset off, which disturbs the experience. This can also cause discomfort which is likely to be counterproductive for health and wellbeing applications. If a user senses an unpleasant fragrance using the system object of the present invention, the user can simply move his or her hand/arm or head away moving the fragrance zone and smelling zone away from another.

Such provisions have no delay, since the fragrance does not have to be actuated, or released. The fragrance is always released naturally. In these embodiments, the fragrance is presented passively, in a manner that reflects a "real-world" fragranced article represented by the delivery device and associated fragrance(s).

Such provisions have the ability to present the user with an unfragranced control (e.g. a blotter, a reed, an unscented towel without fragrance). This is critical in consumer evaluation studies.

Such provisions represent the way that perfumers/creators/consumers already interact with fragrance and fragranced articles on a daily basis: i.e. passively without actuating, spraying, the use of fans, heaters (these would only be used in case this represents a real-life scenario. For example, having a heater to gently warm up artificial skin to 32° C. would be a good way to further improve the fidelity of a fragrance evaluation on skin).

Such provisions are very suitable for users to rate the fragrance experienced using a star or point rating (e.g. 1-5 stars, rating 1-10).

Such provisions are for people to show purchase intent.

Such provisions allow for greater fragrance fidelity, allowing for higher fidelity user interaction monitoring.

In particular embodiments, the system object of the present invention further comprises:
- a relative positioning tracker configured to detect the positioning of the portable fragrance device relative a facial feature of a user and
- a data storing means storing data based on the relative positioning detected.

These embodiments allow the tracking of a user's physical behavior relative to a fragrance that can be held and moved around by said user to be monitored. Such interaction monitoring provides valuable modelling opportunities to detect, for example, how much a user appreciates a fragrance or to quantify the strength of a fragrance based on the distance at which the portable device is kept from the face of the user. The collected data can thus be used to determine fragrance performance indicators.

As the fragrance device is tracked, preferably in a three dimensional referential, allowing the user to bring the fragranced article to one's nose to evaluate the character, intensity and other quality attributes of a fragrance with great fidelity, while data is collected on a user's gestures during the experience.

In particular embodiments, the system object of the present invention further comprises a virtual spatial fragrance zone modeling means configured to define a virtual volume in proximity of the fragrance delivery device, the relative positioning tracker being configured to detect the positioning of the virtual spatial fragrance zone relative to the tracked facial feature.

Such embodiments allow for more precise interaction data collection as the fragrance detection zone is modelled, this in turn allows greater precision than the monitoring of the interactions of the user with the device as such.

In particular embodiments, the system object of the present invention further comprises a virtual user smelling zone modeling means configured to define a virtual volume in proximity of the tracked facial feature, the relative positioning tracker being configured to detect the positioning of the portable fragrance device or the virtual spatial fragrance zone relative to the virtual user smelling zone.

Such embodiments allow for more precise interaction data collection as the fragrance detection zone of the user, that is the zone around the nose, is modelled. This in turn allows greater precision than the monitoring of the interactions of the user's face as such.

In particular embodiments, the system object of the present invention further comprises a user gesture detection means, the data stored corresponding at least in part to the detected user gesture.

Such embodiments allow not only to store positioning data, but also allow to store user gesture representative data. The determination of said gestures depends on the type of gesture to monitor.

In particular embodiments, the user gesture detection means is configured to detect a gesture corresponding to a smelling event by the user, such event being detected as a function of a distance between the detected positions of the facial feature and the portable fragrance device.

In particular embodiments, the system object of the present invention further comprises a relative position evolution measurement means configured to determine, over time, the position of the portable fragrance delivery device relative to the position of the facial feature, the user gesture detection means being configured to detect a user gesture based on the relative position evolution measured.

Such embodiments allow for the determination of gestures based not only on relative positioning, but on the evolution of that positioning over time.

In particular embodiments, the fragrance delivery device comprises a fragrance selector configured to present at least one determined fragrance among a plurality of fragrances.

Such embodiments allow to monitor the interactions of a user on a number of fragrances using only one delivery device.

In particular embodiments, the system object of the present invention further comprises a digital environment event detector in the digital environment, the selector being actuated as a function of the digital event detected.

Such embodiments allow the matching of visual and/or audio stimuli with a given fragrance associated to said stimuli.

In particular embodiments, the digital environment display is configured to be worn on the head of a user, the multisensory system further comprising:
- a spatial position tracking means being configured to track the position of the digital environment display,
- a facial position inference means configured to infer the position of the facial feature based on the digital environment display position tracked.

Such embodiments allow providing visual and audio sensorial input to the user and monitoring the interactions of the user with combined sensorial inputs including more than the fragrance itself. Furthermore, the positioning of the display can be used as a proxy to any part of the face of the user.

In particular embodiments, the system object of the present invention further comprises a robotic arm configured to hold the portable fragrance delivery device.

Such embodiments allow for a more controlled monitoring to take place, limiting the gestures of the users with respect to the delivery device.

In particular embodiments, the portable fragrance delivery device comprises an artificial human body part upon (e.g. artificial skin) or fragranced item representation which the fragrance delivery is performed.

Such embodiments allow for greater fragrance fidelity, allowing for higher fidelity user interaction monitoring.

In particular embodiments, the system object of the present invention further comprises a user body behavior detection means or an ambient physical parameter sensor, such body behavior or an ambient physical parameter being stored by the storing means.

Such embodiments allow for the monitoring of further user or environment parameters.

In particular embodiments, the system object of the present invention further comprises a fragrance physical parameter detection means, the fragrance physical parameter detected being stored by the storing means.

Such embodiments allow for the comparison of user interaction monitoring versus data collected by the physical parameter detection means.

In particular embodiments, the fragrance delivery device comprises several fragrance sources, at least two said sources being separated by a shield.

Such embodiments reduce the risk of cross-contamination.

In particular embodiments, the fragrance delivery device comprises several fragrance sources, at least two said sources are organized along a rotation axis, the system further comprising a rotating housing comprising a slit configured to selectively overlap with at least one fragrance source depending on the rotation angle of the said housing.

Such embodiments reduce the risk of cross-contamination.

In a fourth aspect, the present invention aims at a multi-sensory experience method comprising:
- a fragrance delivery step operated by a passive and portable fragrance delivery device,
- a delivery device position tracking step,
- a delivery device position conversion step to convert the tracked position of the device into a virtual environment position and
- a digital environment display step comprising a modeling step to model, in the digital environment, a virtual image in a position corresponding to the tracked delivery device.

The advantages of said method correspond to the respective system.

BRIEF DESCRIPTION OF THE DRAWINGS

Other advantages, purposes and particular characteristics of the invention shall be apparent from the following non-exhaustive description of at least one particular systems and methods which are object of this invention, in relation to the drawings annexed hereto, in which.

DETAILED DESCRIPTION OF THE INVENTION

This description is not exhaustive, as each feature of one embodiment may be combined with any other feature of any other embodiment in an advantageous manner.

It should be noted at this point that the figures are not to scale.

Note that the term "portable" refers to any device that can be picked-up and carried by a user using one's hand. Another way to define "portable", in the particular instance of the aim of this invention, is to consider that portability is achieved when the portable device can be moved independently of the user. This means for example, that the movement of the head does not translate into a proportionate movement of the portable device. Portability is achieved, for example, when the device can be picked-up, dropped, positioned or when the device is not attached to the user.

Another way to define "portable" is to define a portable device as being capable of being transported or conveyed. Said portable device does not require to be necessarily held all the time, but has the ability to be easily picked up. For example, an electrical plug-in air freshener requiring to be plugged into an electrical outlet can be considered as portable.

Figure 7:
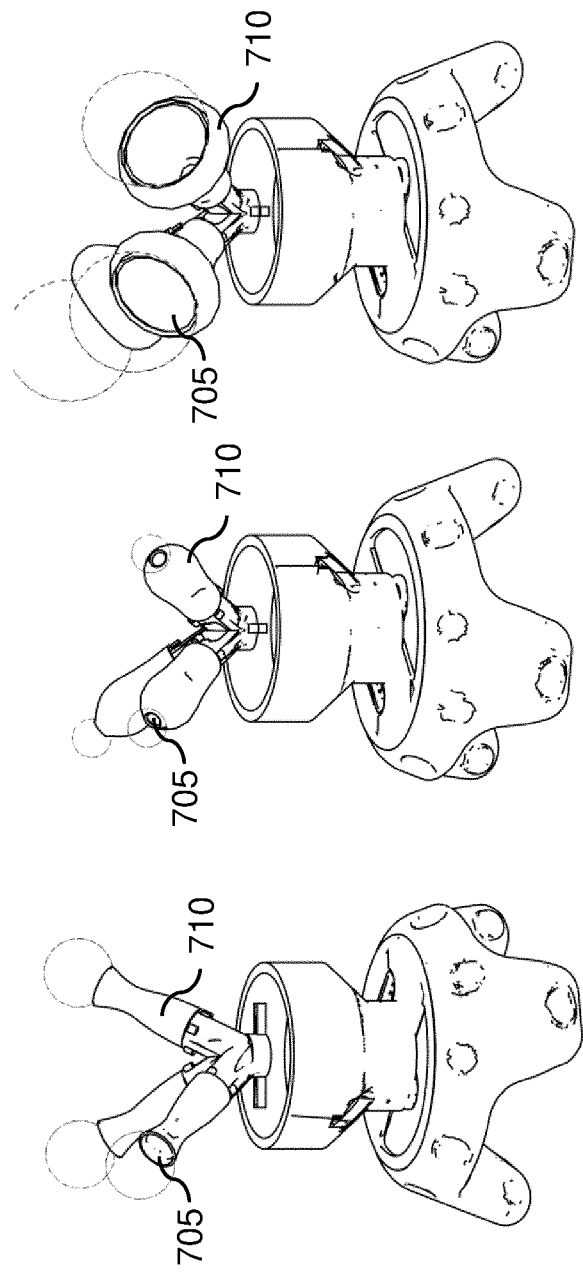
FIG. 7 represents, schematically, a third embodiment of a fragrance delivery device of a system object of the present invention.

For example, FIG. 7 shows what could be a situation where three separate fragrance delivery devices are available that could be picked up one at a time and put back on a table or in another position in a room. In a particular scenario, a user picks up a relative/absolute position tracked air freshener, opens it, sniffs it and then places it in a room. One could study for example if the strength or character of the fragrance determines if the user will position it in a bathroom or living room, and the distance from the toilet for example. The device is portable but then it is positioned according to its intended use.

The term "facial feature" refers to any part of the face or the entirety of the face of the user. Preferably, the facial feature considered is the nose of the user. Depending on the nature of the data to be collected, other parts of the face of the user can be targeted.

The term "gesture" refers to any element of movement, or gestural activity, which includes any movement of limbs, head, hands, torso, etc. For example, a gesture might refer to the acts of grabbing and bringing forth a fragrance delivery device to one's nose.

Figure 1:
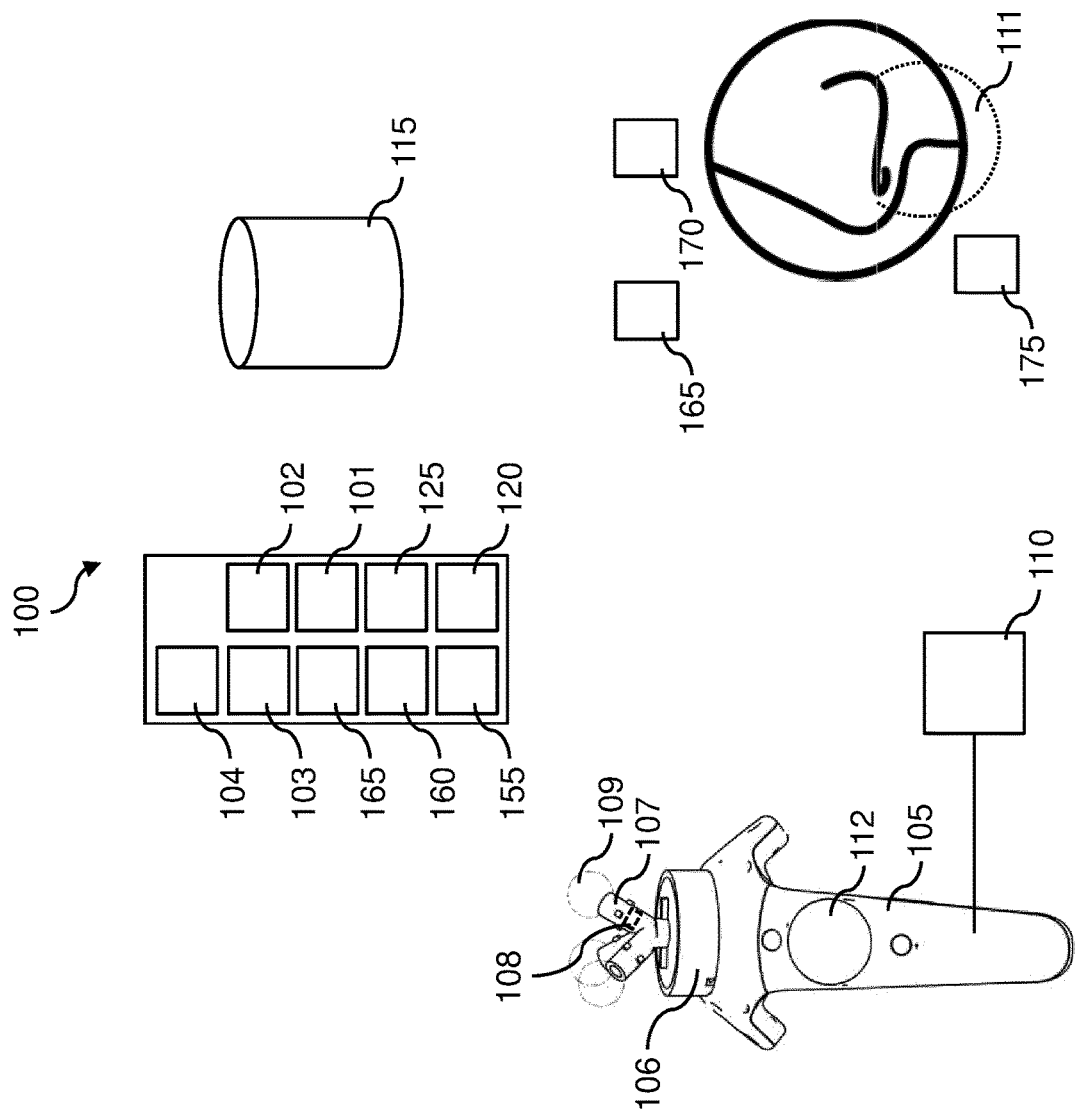
FIG. 1 represents, schematically, a first embodiment of a system object of the present invention.

FIG. 1, which is not to scale, shows a schematic view of a system which is the subject of this invention. This user gesture data collection system 100 comprises:
- a portable fragrance delivery device 105,
- a relative positioning tracker 110 configured to detect the positioning of the portable fragrance device relative a facial feature of a user and
- a data storing means 115 storing data based on the relative positioning detected.

The portable fragrance delivery device 105 is defined by its capacity to deliver a fragrance, thus the particular nature of fragrance delivery mechanism to be used depends on the intent of the designer of the system 100.

In particular embodiments, not represented in the figures, the fragrance delivery device 105 comprises an active fragrance delivery means. The term "active" designates fragrance delivery mechanisms which provide airflow generation or fragrance projection means. Such airflow generation or fragrance projection means can be, for example, fans, dispensers or pumps creating an airflow put in contact with a fragrance stemming from a solid, gaseous or liquid source. Such embodiments are only preferred when the fidelity of the fragranced article to be emulated requires it. For example, if an air freshener under evaluation uses a fan, then the delivery device 105 can provide an equivalent fan.

In other particular embodiments, such as represented in FIG. 1, the fragrance delivery device 105 comprises a passive fragrance delivery means 107. The term "passive" designates, by opposition to "active fragrance delivery", delivery mechanisms in which natural diffusion/convection of the fragrance, without airflow generation or fragrance projection means, allows for the fragrance to spread spatially. A passive fragrance delivery means 107 aims at reproducing the real-life sensation occurring while smelling a fragrance in which the fragrance is naturally present in the area surrounding its source, even in the absence of airflow surrounding said source.

Such a passive delivery means 107 can be, for example, a blotter, wick or fragrance strip upon which a fragrant liquid has been deposited. Other variants of said passive delivery means 107 are swatches representative of another fragrant item.

There are many formats in which fragrances or delivery device 105 can be presented to the user. Preferred are the formats that maintain the fidelity of the fragrance that the perfumer intended. Therefore, the tools-of-the-trade that experts in the field use are most preferred or the actual finished product or acceptable swatches of these (e.g. a wick, a paper blotter, a fragrance marker, a piece of fragranced candle wax, a liquid detergent cap, a skin patch (i.e. artificial skin) or air freshener reeds). Other non-limiting examples include hair swatches and/or fabric swatches to evaluate different shampoos or fabric softeners. Here even the sensation of hair or fabric touching the nose can enhance the perception of actually smelling fragrances as intended.

Figure 6:
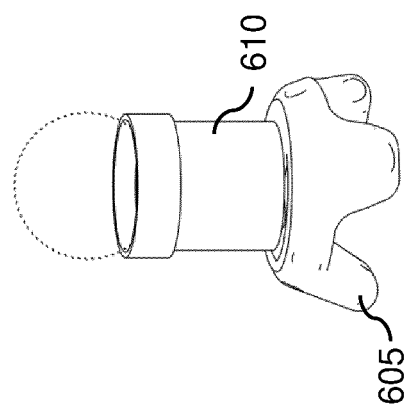
FIG. 6 represents, schematically, a second embodiment of a fragrance delivery device of a system object of the present invention.

An example is shown in FIG. 6 of a fragranced laundry detergent cap 610 connected to a tracker 605 that can be screwed on top of a laundry detergent bottle or can be presented by itself ready for sniffing. Since the cap 610 is connected to a tracker 605, the user would be able to use their hands to pick up this device and bring it to their nose for evaluation.

In particular embodiments, the system 100 comprises more than one delivery device 105.

In particular embodiments, the delivery devices 105 comprises retractable wicks, or lipstick type of devices that can be moved to expose a larger surface area of a wick without ever truly turning the device off. However, this tweaking of intensity should never detract from the fidelity of the fragrance. This could be requested by the user in the experience but may also be governed by ambient conditions. E.g. as the temperature in a room rises, the vapor pressure of liquids increases hence the exposed surface area should be reduced to have the same fragrance intensity between several users.

In particular embodiments, the delivery device 105 can further comprise user entry means, such as a touchpad on a VR controller. Such entry can represent a rating of the fragrance's intensity, its perceived quality, the user's preference or evaluate the character, possibly over time.

The relative positioning tracker 110 is defined by its capacity to measure a distance between the fragrance delivery device 105 and the user's designated facial feature. Preferably, the facial feature tracked is the user's nose. The position of the user's nose can either be detected or inferred based on other collected data, such as the recognition, in an image, of another facial feature of a user, knowing the typical distance between said facial feature and the nose. Such inference-based mechanisms can use existing datasets to create said inference models.

In other variants, the nose location is predicted based on the location of the headset. For example one could use knowledge on the 3D location of someone's eyes to provide an estimate of the nose location based on the Euclidian distance estimations used for example in 3D face recognition methodologies (e.g. Berretti, S., del Bimbo, A., Pala, P. 3D Face Recognition Using Spatial Relations, Chapter 12, 679 In Computer Vision: Concepts, Methodologies, Tools, and Applications: Concepts, Methodologies, Tools, and Applications Management Association, Information Resources IGI Global, Feb. 2, 2018).

There are many ways to embody said relative positioning tracker 110.

In a first particular embodiment, the relative positioning tracker 110 is a part of the fragrance delivery device 105. In such an embodiment, the tracker 110 can measure distance via measurement of the Doppler effect of a wave sent in direction of the user's face. The nature of the wave and particular implementation is not limiting insofar as the Doppler effect is measurable as the tracker 110 is approached from the user's facial feature. In such an embodiment, the tracker 110 can be a Doppler radar.

In a variant, the tracker 110 can be a heat sensor in proximity of the fragrance delivery device 105. As the heat grows, an inference can be made regarding the likely distance of the facial feature of the user.

In a second particular embodiment, the relative positioning tracker relies on image processing. In such an embodiment, the tracker comprises an image sensor, such as a camera or video camera, and an image processing unit, such as an image processing software ran by computing means. The image processing unit is configured to detect, within the sensed image, the user's facial feature—via facial recognition for example—and the delivery device 105—via shape recognition for example. From the detection of such items, their positions in space can be determined and thus the relative distance between said items can be calculated. Such an embodiment can be applied to both image and video recording.

In a third particular embodiment, the relative positioning tracker comprises:
 a first spatial position tracker of the fragrance delivery device 105, for example an electromechanical gyroscope attached to the delivery device 105 and
 a second spatial position tracker of the facial feature, for example an electromechanical gyroscope attached to the head of the user such as in a VR headset.

From the acceleration measurements of each gyroscope, the position of each item can be measured. From said positions, distance can be measured, and thus relative positioning can be determined. To allow for less positioning error, the delivery device 105 and the gyroscope to be attached to the head of the user can be positioned in an initial predetermined location, each location having predetermined position coordinates.

Figure 2:
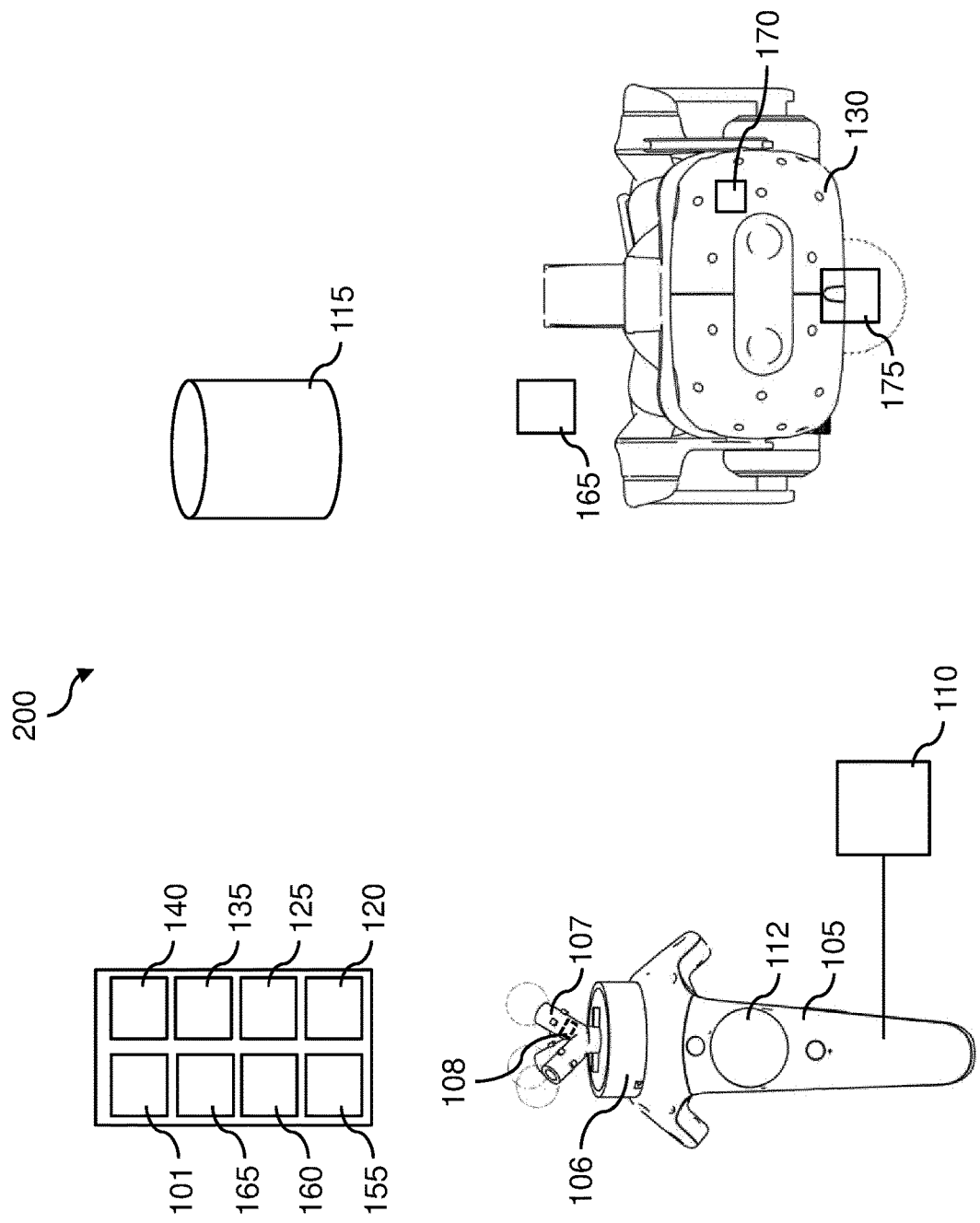
FIG. 2 represents, schematically, a second embodiment of a system object of the present invention.

In variants of this third embodiment, such as shown in FIG. 2, the fragrance delivery device 105 can be mounted upon a VR system controller spatially located by a first spatial position tracker and a second spatial position tracker can be configured to track the position of a VR headset.

The exact nature of said spatial position trackers depends on the technology used for the VR system. For example, base station infrared emitting laser beams to locate the VR headset and controller such as used by the HTC Vive (Trademarked).

In particular embodiments, the relative position tracker is configured to determine the positioning, orientation, speed and/or acceleration of the delivery device 105 and/or of the facial feature either in absolute or relative terms to one another.

Figure 5:
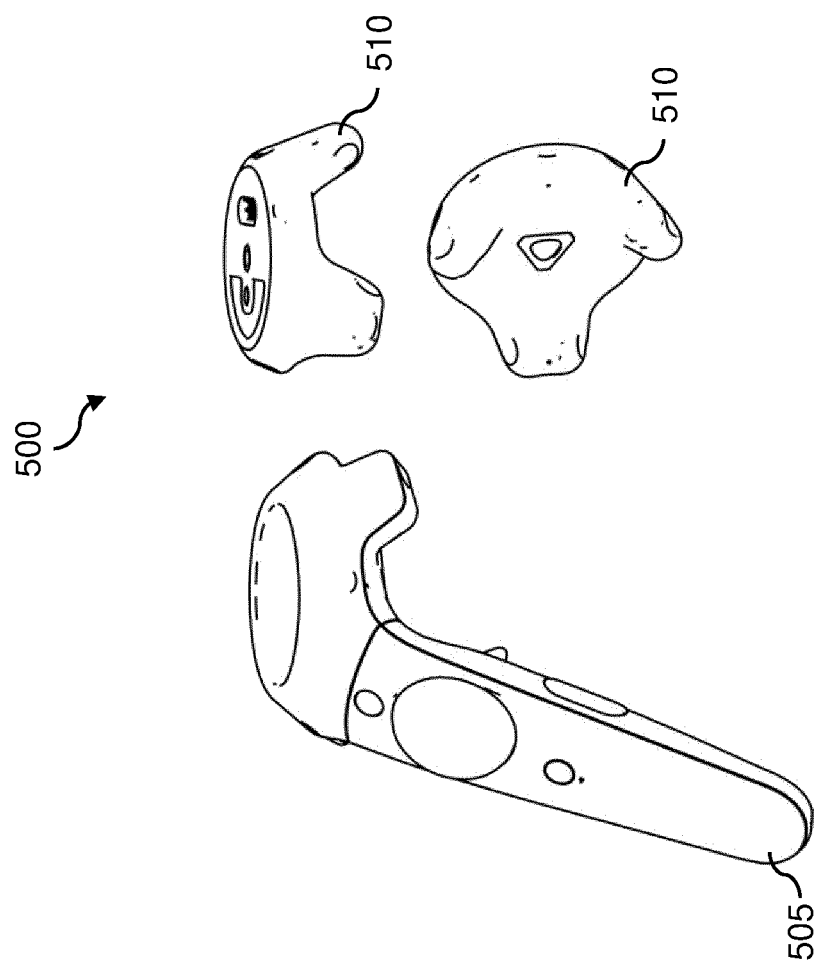
FIG. 5 represents, schematically, a first embodiment of a fragrance delivery device of a system object of the present invention.

FIG. 5 shows a particular embodiment of a delivery device tracking system 500. Such a system 500 comprises:

a handheld controller 505 comprising a relative position tracker, which can receive a fragrance or fragranced article, for a user to handle and a relative positioning tracker 510, which can receive a fragrance or fragranced article, shown at two different angles.

The relative position can be tracked in terms of spatial coordinates (location), angle of movement and/or speed of movement. The tracking can be performed on a plane or in a three-dimensional (3D) space. The tracking can be performed in real-time.

In particular embodiments, the delivery device 105 is tracked both 3D space and in time, such that it is visible to the user in a VR system and allows the positioning, orientation, speed and/or acceleration of the delivery device 105 to be recorded in real-time. This includes any system that allows the delivery device 105 to be tracked in space and time. The data storing means 115 is, for example, a database configured to store, in a computer memory, data provided by the relative positioning tracker 110. Such data storing means 115 can be on premise, accessible on the cloud or hybrid, that is comprising both on premise and on the cloud capabilities.

The exact nature of the data storing means 115 depends on the use intended for the system 100.

The data stored can then be used to model the user's behavior relative to the fragrance delivered. Such modeling can be used as a performance indicator of a targeted fragrance.

Figure 3:
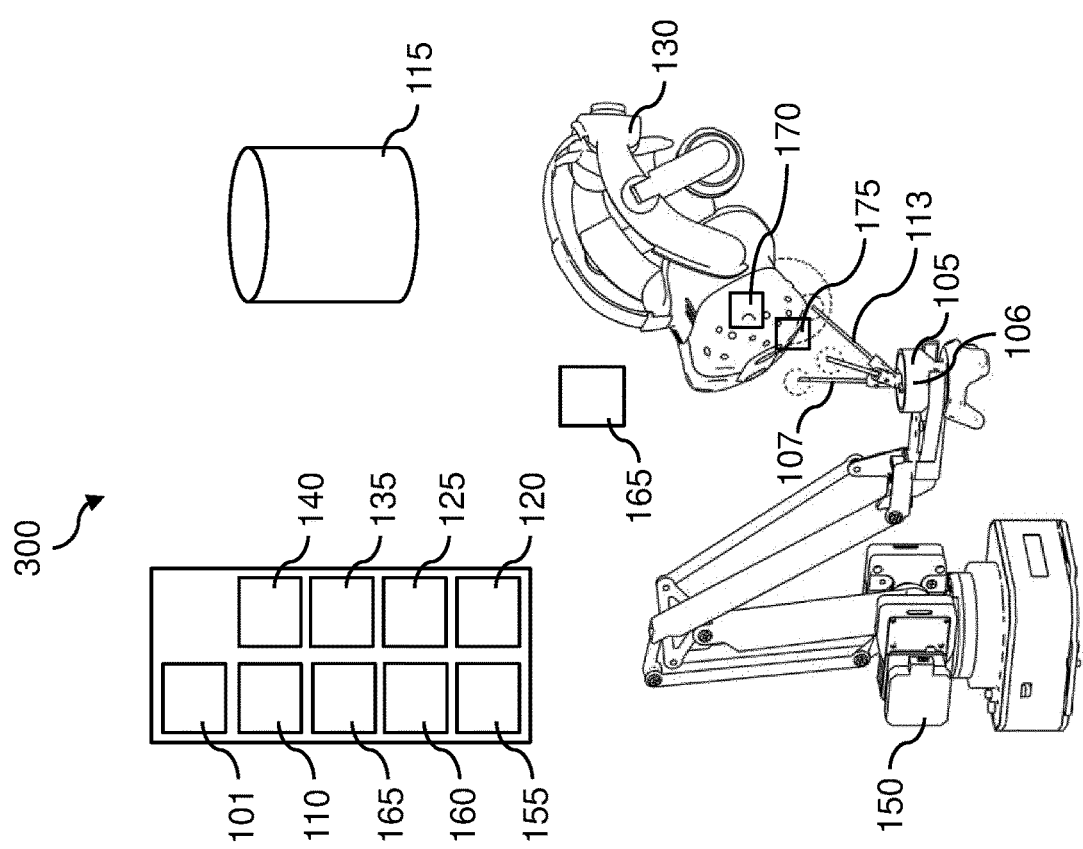
FIG. 3 represents, schematically, a third embodiment of a system object of the present invention.

In particular embodiments, such as shown in FIGS. 1 to 3, the system 100 further comprises a virtual spatial fragrance zone modeling means 120 configured to define a virtual volume in proximity of the fragrance delivery device 105, the relative positioning tracker 110 being configured to detect the positioning of the virtual spatial fragrance zone relative to the tracked facial feature.

The fragrance zone modeling means 120 is, for example, a computer program ran on a computing system. Said computer program is configured to fit, at the position of the fragrance or, by proxy, of the delivery device 105 a volume of a particular shape, such as a sphere or a cone for example.

Such a fragrance zone 109 is shown in FIG. 1.

In more perfected variants, the position of the fragrance delivery location is known or determined and the shape delimiting the fragrance zone is positioned relative to the fragrance delivery location. For example, if the delivery device 105 is located on a VR system controller in a given location, the position and orientation of the VR system controller in space make it possible to know the fragrance delivery location.

The fragrance zone defines a 3D space in which fragrance is present at perceivable concentrations by the user. This zone can be spherical, conical or any other shape, it can be very small converging into a point or can be very large (the size of a room or beyond). For example, for each fragrance there may be an ideal location to hold the fragrance delivery device 105 to maximize fragrance concentration near the nose. This ideal location could be predicted and shown in a VR, AR or MR system. Such systems could further comprise, for example a voice emitter delivering a message corresponding to "move your hand to this location to smell the fragrance" and the location could be shown as a target in 3D space.

It is also conceivable that close-to-skin formulations are particularly suited for providing a fragrance experience to one's personal space without disturbing others with unwanted fragrance, e.g. airplane, hospital bed. This is especially relevant for health and well-being applications. In this example, the delivery device 105 could comprise shields with very small openings, and then the fragrance zone would be considerably smaller.

In particular embodiments, such as shown in FIGS. 1 to 3, the system 100 comprises a virtual user smelling zone modeling means 125 configured to define a virtual volume in proximity of the tracked facial feature, the relative positioning tracker 110 being configured to detect the positioning of the portable fragrance device 105 or the virtual spatial fragrance zone relative to the virtual user smelling zone.

A smelling zone refers to a virtual zone corresponding to a real-life fragrance smell detection zone by the user.

The smelling zone modeling means 125 is, for example, a computer program ran on a computing system. Said computer program is configured to fit, at the position of the facial feature a volume of a particular shape, such as a sphere or a cone for example.

Such a smelling zone 111 is shown in FIG. 1.

When the delivery device 105 is away from the user's nose, the fragrance concentration is too dilute to be perceived and may generally be outside the user's smelling zone.

The size, shape and position of such a smelling zone 111 can vary depending on the nature of the fragrance associated to the delivery device 105.

In other variants, size, shape and position of such a smelling zone 111 can result of a smelling zone calibration means. Such a calibration means, for example a calibration software, can present the user with a number of fragrance and require input of the user on whether or not the user is able to detect said fragrance. Each fragrance is associated to a nominal smelling zone and thus an indicator of the capacity to detect fragrances of the user can be derived and applied to other nominal smelling zones of fragrances.

In particular embodiments, such as shown in FIG. 1, the system 100 further comprises a user breathing cycle modeling means 101, the user smelling zone being defined as a function of the modelled breathing cycle.

Such a breathing cycle modeling means 101 is, for example, a computer program executed upon an electronic computing means. Such a breathing cycle modeling means 101 can consist, in particular embodiments, in the computation of fluid dynamics incurring when a human being inhales or exhales around the nose of said human being. Such a prediction can then be used when defining the smelling zone so that this smelling zone is made dynamic in its dimensions. The parameters of such a computational fluid dynamics can readily be found in scientific publications, such as Bates, A. J.; Doorly, D. J.; Cetto, R.; Calmet, H.; Gambaruto, A. M.; Tolley, N. S.; Houzeaux, G.; Schroter, R. C., Dynamics of airflow in a short inhalation. J R Soc Interface 2015, 12 (102), 20140880-20140880.

In such embodiments, a breathing cycle detection means (not represented) may be used. Such a breathing cycle detection means is, for example, an airflow sensor mounted upon a headset. In other variants, the breathing cycle detection means is a logical or physical actuator activated by the user at a moment corresponding to a specific time in the breathing cycle (start of inhalation for instance).

A logical actuator may correspond to, for example, a virtual element of a graphic user interface that may be activated by a human-machine interface, such as a handheld controller of a VR system associated to the display of a trigger upon the electronic display of that VR system.

In embodiments which comprise a selector 106, the selection of a fragrance can correspond to the selection of an associated virtual fragrance zone to be modelled and used by the current system 100.

A virtual indicator in the virtual world could indicate where a user should position his/her nose to evaluate the fragrance. This feature is important to ensure correct positioning of the user, or representative fragrance zone and the smelling zone. Correctly positioning this virtual indicator (for example as a small sphere) ensures obtaining good compliance of positioning the device in the correct location below the nose.

In particular embodiments, such as shown in FIGS. 2 and 3, the system, 200 or 300, further comprises:
- a digital environment display 130 configured to be worn on the head of the user,
- a spatial position tracking means 135 being configured to track the position of the digital environment display,
- a facial position inference means 140 configured to infer the position of the facial feature based on the digital environment display position tracked.

The digital environment display 130 is, for example, a VR, AR or MR display integrated into a headset—that is a head-up wearable device. This display projects digital images in either a virtual or real environment depending on the technology. Such images can represent, for example, images corresponding to the fragrances delivered by the delivery device 105.

The spatial position tracking means 135 corresponds to one of the alternatives described above in relation to the relative position tracker 110 when considering tracking a VR headset.

The facial inference means 140 is, for example, a computer program ran on a computing system. Said computer program to offset, by a determined value, the position of the display 130 to obtain the position of the facial feature. For example, if the display 130 is intended to be worn partly on the nose and the position of the display, the position of the nose can be inferred based on the position of the display 130.

In particular embodiments, the portable fragrance delivery device 105 comprises a fragrance selector 106 configured to present at least one determined fragrance among a plurality of fragrances.

It is often preferred to present multiple samples to a user in fairly rapid succession and it is convenient to have a universal device that allows for one or multiple fragrances to be presented. For example, one may want to have a user evaluate the dry down of a fine fragrance on a blotter. One could prepare one blotter 12 hours before the demo, one 6 hours before the demo and one right before the demo and position them in three slots of the delivery device 105, such as shown in FIG. 1. The user can now quickly evaluate the difference in character over time. While the virtual reality environment, could for example represent the fragrance in a fictional setting representing a morning, afternoon and evening setting, where the user could quickly switch between the different times of day interactively, while rating and evaluating each fragrance successively.

The selector 106 could use different fragrance delivery positions that allows the separate presentation of samples to a user for evaluation. The different fragrances can either be evaluated by rotating the device manually and bringing the fragrance to one's nose or by rotating one head over the fragrance source and positioning one's head around the device such that there is an overlap between the fragrance zone and smelling zone. This alternative can be further be aided by an embedded motor that is configured to rotate and present a fragranced source at preset positions.

The fragrance selector 106 can be, for example, a liquid fragrance drop valve confirmed to allow the passage of a fragrant liquid, among several, into a delivery area or delivery means of the delivery device 105.

In variants, the fragrance selector 106 is a valve configured to obtrude the airflow in a fragrance delivery conduit located between the fragrance source and a smelling zone for the user. Such selective obstruction allows for the selection of fragrance that the user can smell.

In case of suspected likely contamination, the fragrance sources can be separated by a shield with an opening at the top that—much like a wine glass—allows the fragrance to be concentrated, contained and separated from the environment while providing a defined opening at the top where the fragrance can be sniffed.

Three examples of such openings 705 and shields 710 are shown in FIG. 7.

The proper selection and use of these shields negate the need for exhaust systems, fans and other means to dilute or extract any presented fragrance.

Figure 8:
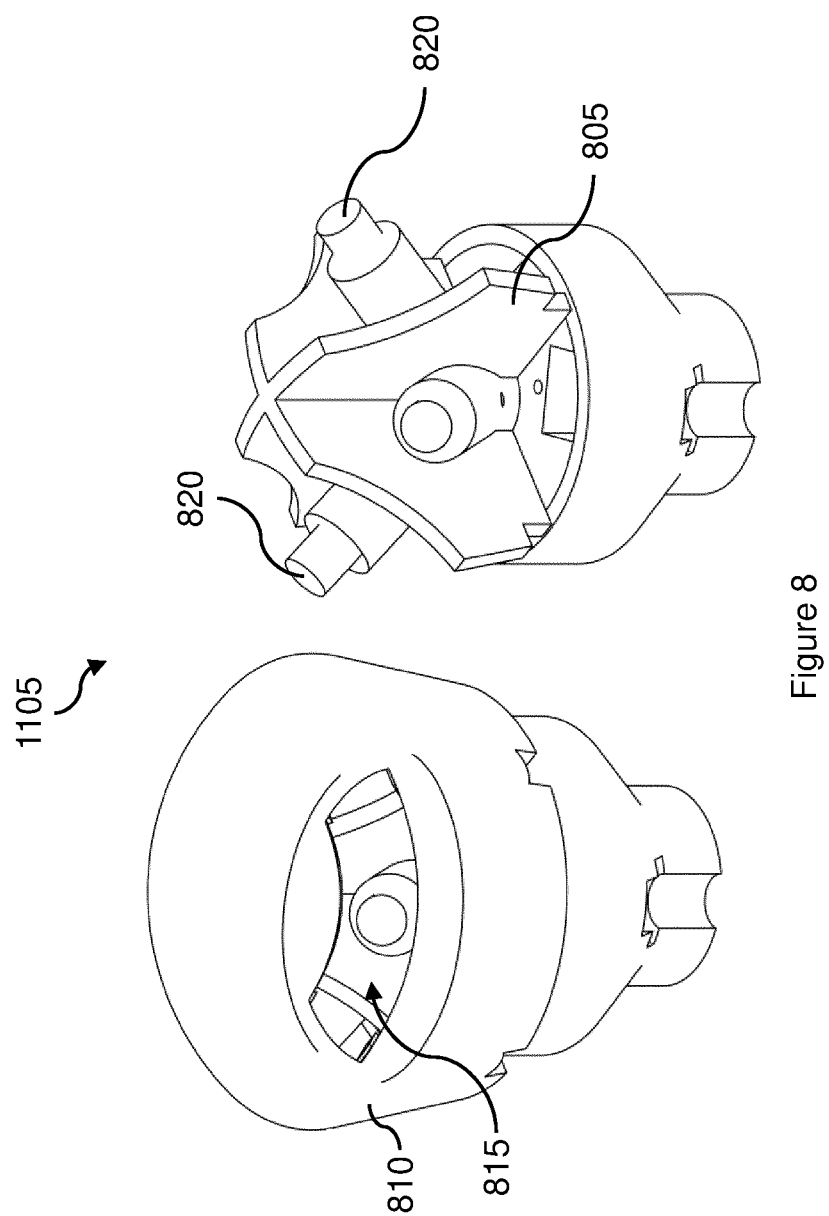
FIG. 8 represents, schematically, a fourth embodiment of a fragrance delivery device of a system object of the present invention.

Furthermore, contamination could be further negated providing walls 805 separating individual fragrances, such as shown in FIG. 8.

Furthermore, contamination could be further negated by providing a dome 810 with a slit 815 that only allows one prong or sample to protrude from the dome 810, such as shown in FIG. 8.

Figure 11:
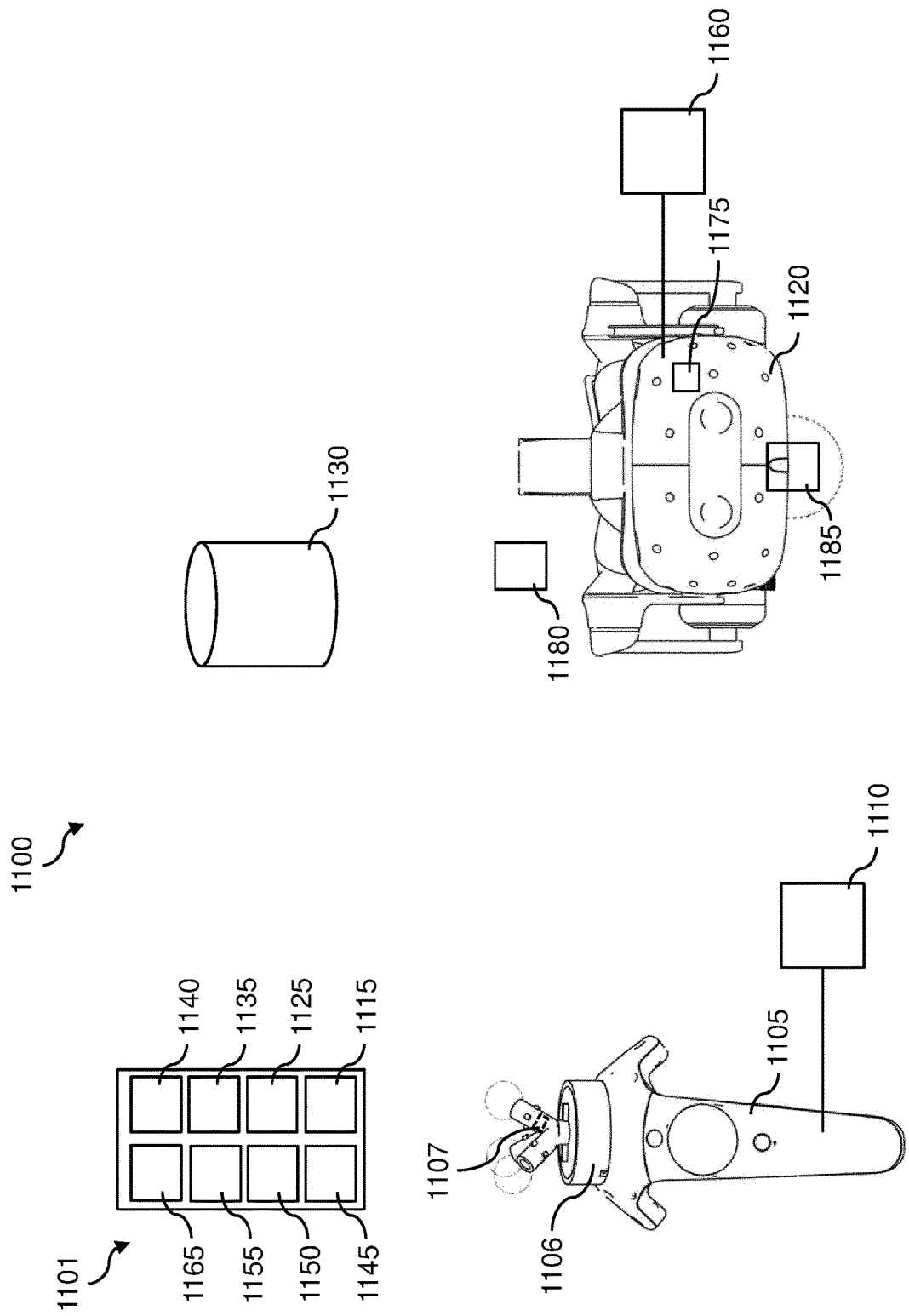
FIG. 11 represents, schematically, a fourth embodiment of a system object of the present invention.
Figure 12:
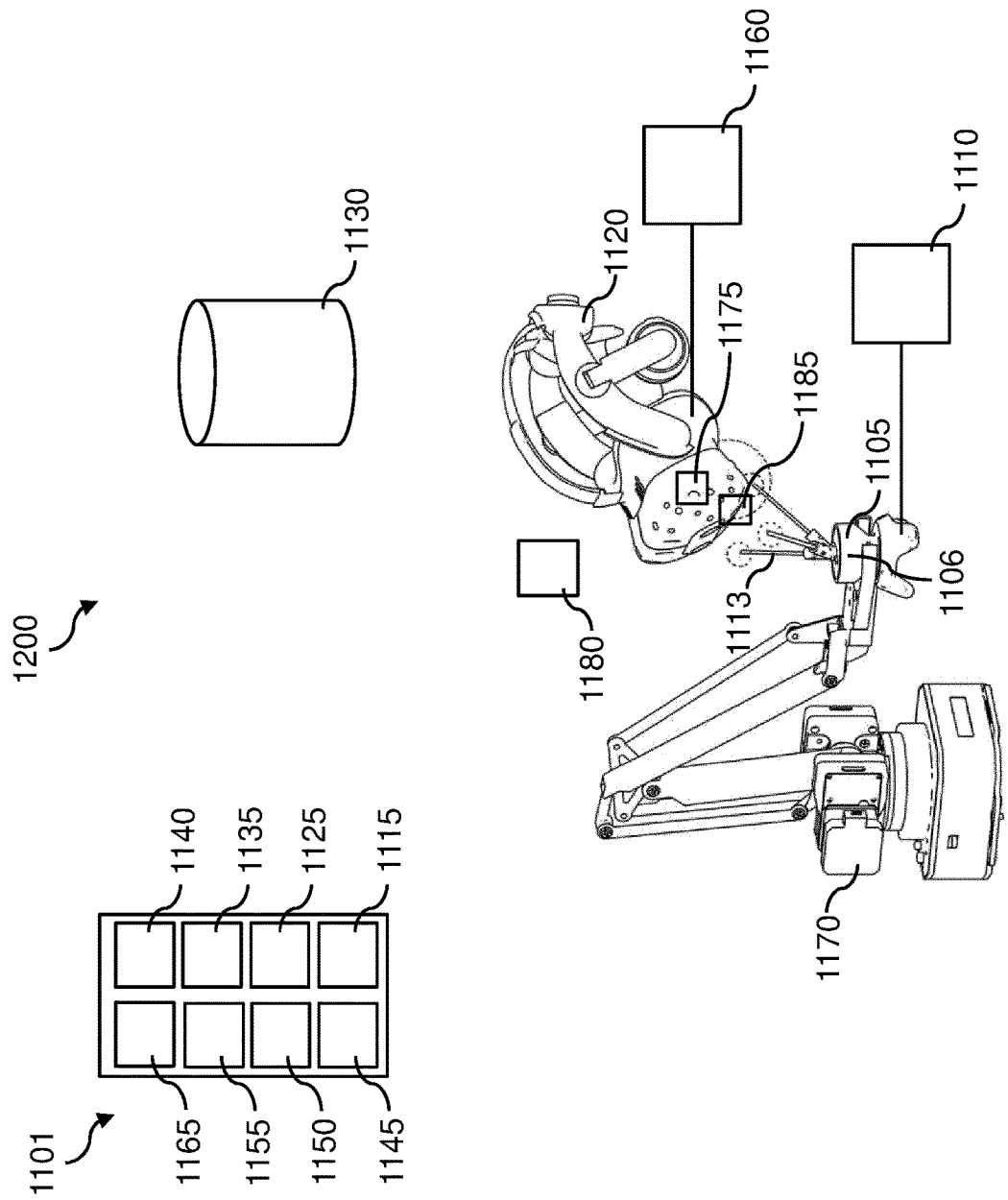
FIG. 12 represents, schematically, a fifth embodiment of a system object of the present invention.

As it is understood, FIG. 8 shows a system in which the fragrance delivery device 1105, of FIGS. 11 and 12 for example, comprises several fragrance sources 820, at least two said sources being separated by a shield 805.

In this system, the sources considered are wicks associated to fragranced articles located within, for example. Such wicks may be incorporated within a shield. Said shield can have the general shape of a cylinder, for example, such as seen in FIG. 7.

As it is understood, FIG. 8 shows a system in which the fragrance delivery device 1105, of FIGS. 11 and 12 for example, comprises several fragrance sources 820, at least two said sources are organized along a rotation axis, the system further comprising a rotating housing 810 comprising a slit 805 configured to selectively overlap with at least one fragrance source 820 depending on the rotation angle of the said housing 810.

In particular embodiments, such as shown in FIGS. 2 and 3, the system, 200 and 300, comprises a digital environment event detector 145, the selector 106 being actuated as a function of the digital event detected.

The digital environment event detector 145 is, for example, a computer program ran on a computing system. Such a computer program can vary in execution and essentially consists in the detection of an action performed in a virtual environment by the user or any other source. Such an action can be, for example, the user picking up a flower in the digital space.

Upon the detection of such an event, the selector 106 can be actuated to select an appropriate fragrance for the user to smell.

In particular embodiments, such as shown in FIG. 3, the system 300 comprises a robotic arm 150 configured to hold and move the portable fragrance delivery device 105.

Such a robotic arm 150 could be movable in 3D. This robotic arm 150 can comprise a 3D tracker or other means by which the spatial position of the delivery device 105 is known, possibly in real-time. This robotic arm 150 could move and position a delivery device 105 in defined locations. This robotic arm 150 could also serve as a virtual assistant, presenting a user with multiple fragrances. Optionally this robotic arm 150 could be separated from the user by a protective screen with a slit that allows samples to protrude.

A non-limiting example is a 'virtual fragrance assistant', a robotic arm 150 in real life that picks up fragrance blotters that are dipped in various fragrance liquids. The user can choose from a wide array of liquids, which the robotic arm 150 then dips and presents to the user. The robotic arm 150 may have a tracker on itself, but this system maybe redundant with its built-in three-dimensional positioning data tracking.

In another embodiment, the robotic arm 150 is mounted upon a track and mobile along the path created by said track. Depending on the shape of the track, it is possible to create a fixed user-device interaction sequence to be used as a testing step of a fragrance performance evaluation. Such a test could be, for example, used to determine the evolution of a moving fragrance over time.

In particular embodiments, such as shown in FIGS. 1 and 2, the portable fragrance delivery device 105 comprises an artificial human body part 108 upon which the fragrance is applied.

Such an artificial human body part can be, for example, a hair or skin simulacrum.

In variants, the portable fragrance delivery device 105 comprises a fabric upon which the fragrance delivery is performed.

In variants, the portable fragrance delivery device 105 comprises an item representation 113. Such an item representation corresponds to a real-life item usually associated with the fragrance delivered. For example, this item representation can be a detergent bottle cap or bottle.

In particular embodiments, such as shown in FIGS. 1 to 3, the system, 100, 200 and 300, comprises a user gesture detection means 155, the data stored corresponding at least in part to the detected user gesture.

The term "gesture" refers to a visible bodily action performed by the user in interaction with the delivery device 105. Such a gesture can be, for example, smelling the fragrance by bringing the delivery device 105 close to one's nose or pushing back the delivery device 105. A gesture can correspond to a head, arm or hand movement, for example.

For example, the user would use their gestures or movements to have the fragrance zone and smelling zone collide or intersect, which could in turn trigger a "smelling event". Obviously, other zone evaluation signals, such as position, length of movement, duration of movement, and interpretation of said signals as triggers can be used. This could be done by bringing the fragrance to one's nose using one's hand and arm gestures (e.g. smelling a cut flower that one would bring to one's nose). Alternatively, one could do this by moving one's nose towards the delivery device 105 (as moving one's head to smell a rose on a bush) and one would tune the desired intensity primarily by the distance between one's nose and the delivery device 105.

All of these gestures can be recorded and are meaningful since the natural manner of smelling these objects is preserved, depending on the embodiment of the delivery device, not simulated using fans, actuators, valves, etc.; the user is actually smelling the real fragranced object or a representative swatch or sample as is commonly done in consumer testing.

The user gesture detection means 155 can be a software ran on a computing system associated or not to a dedicated gesture tracker. In a minimalist embodiment, said software is configured to determine a gesture from one value of the relative positions of the facial feature and the delivery device 105. For example, if the distance between facial feature and delivery device 105 is less than a determined value corresponding to an initial relative positioning of facial feature and delivery device 105, then the gesture detections means 155 can determine that the user has brought the delivery device 105 closer to the facial feature. The gesture detected here is, for example, "delivery device brought closer to face".

In more sophisticated embodiments, the user gesture detection means 155 is configured to detect a gesture corresponding to a smelling event by the user, such event being detected as a function of the relative distance between the facial feature and the portable fragrance device 105.

Such an event can be detected if the relative distance between the delivery device 105 and the facial feature drops below a given value.

Alternatively, in variants, such an event can be detected if the relative distance between the fragrance zone and the facial feature drops below a given value.

Alternatively, in variants, such an event can be detected if the relative distance between the delivery device 105 and the smelling zone drops below a given value.

Alternatively, in more complex variants, such an event can be detected if the relative distance between the fragrance zone and the smelling zone drops below a given value.

In these last variants, such a relative distance corresponds, for example, to the intersection of said zones.

In particular embodiments, such as shown in FIGS. 1 to 3, the system, 100, 200 and 300, comprises a relative position evolution measurement means 160 configured to determine, over time, the position of the portable fragrance delivery device 105 relative to the position of the facial feature, the user gesture detection means 155 being configured to detect a user gesture based on the relative position evolution measured.

The relative position evolution measurement means 160 is, for example, a software ran by a computing system configured to monitor and store the evolution of the relation positions of the facial feature and of the delivery device 105 over time. Said user gesture detection means 155 evaluates an evolution parameter, such as a derivative function of the relative position evolution or a threshold comparison to determine the gesture of the user.

For example, if the delivery device 105 or corresponding fragrance zone enters the headspace of the user in a very brief manner and as a part of a continuous movement, the gesture detected can be "hand movement not relative to a smell event".

In particular embodiments, such as shown in FIGS. 1 to 3, the system, 100, 200 and 300, comprises a user body behavior detection means 165 or an ambient physical parameter sensor 170, such body behavior or an ambient physical parameter being stored by the storing means 115.

The user body behavior detection means 165 can be, for example:

a gaze or eye location/direction of the user (up and down) sensor,
a sensor detecting the blinking by the user or
a biometric sensor.

The ambient physical parameter sensor 170 can be, for example, a temperature, humidity, light intensity or airflow sensor.

In particular embodiments, such as shown in FIGS. 1 to 3, the system, 100, 200 and 300, comprises a fragrance physical parameter detection means 175, the fragrance physical parameter detected being stored by the storing means 115.

The fragrance physical parameter detection means 175 can be, for example, an electronic nose configured to detect the presence and quantity of a given chemical compound. Preferably, this fragrance physical parameter detection means 175 is located near the nose of the user and can thus be mounted on a VR, AR or MR headset. This allows for the comparison of user declared data versus automatically detected data.

This physical parameter detection means 175 can be 3D trackable. A 3D dimensional zone that is sampled in real-time using a sensing instrument such as an electronic nose, a VOC (for "Volatile organic compounds") detector or any other instrument that allows for quantification, optional separation or optional identification of flavors, fragrances, malodors or other olfactory substances in a gas phase. The exact shape can be any 3D shape and size, but a person skilled in the art of instrumentation would be able to define, measure or predict the shape and size.

Figure 9:
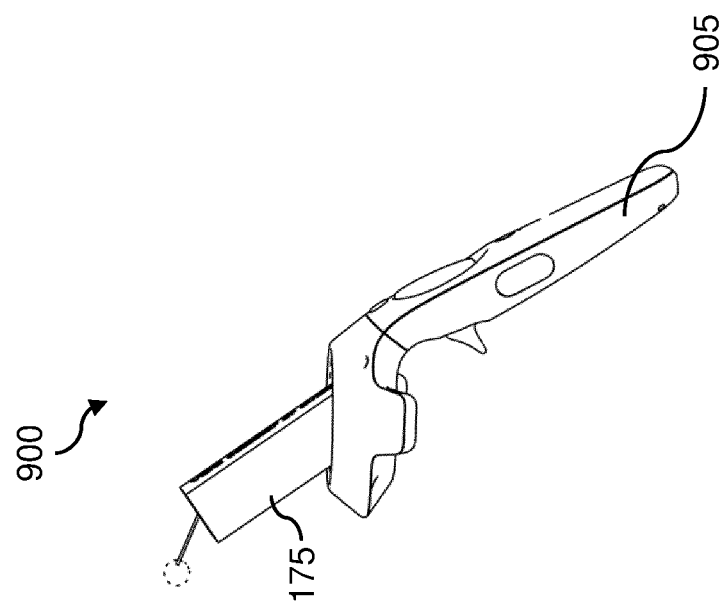
FIG. 9 represents, schematically, a first embodiment of a fragrance physical parameter detection means of a system object of the present invention.
Figure 10:
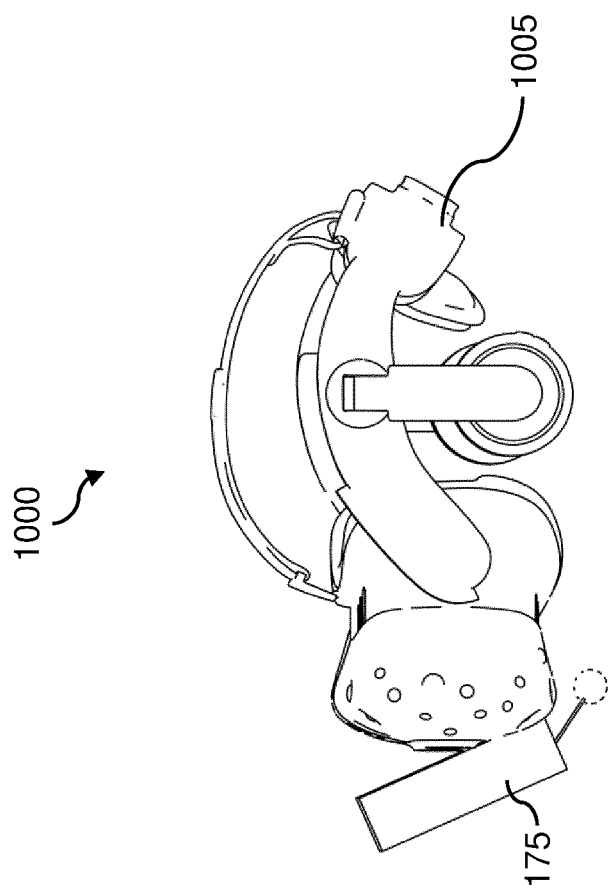
FIG. 10 represents, schematically, a second embodiment of a fragrance physical parameter detection means of a system object of the present invention.

A non-limiting example of such VOC detector is the Tiger Handheld VOC detector (Trademarked) by IonScience (Trademarked). One could easily rigidly connect a VR system controller 905 to this physical parameter detection means 175, such that the sampling location is now known spatially and temporally. Such an embodiment 900 is shown in FIG. 9. FIG. 10 shows an embodiment 1000 in which the physical parameter detection means 175 is mounted on a VR system headset 1005.

In particular embodiments, the system object of the present invention comprises a fragrance spatial mass transfer calculation means 102 and an itinerary definition means 103 configured to determine a route to be followed by an operator as a function of the spatial mass transfer calculated, the relative position tracker 110 being configured to operate in different locations of the route defined.

The fragrance spatial mass transfer calculation means 102 is, for example, a computer program executed upon an electronic computing means. This fragrance spatial mass transfer calculation means 102 may, for example, correspond to an algorithm of computational fluid dynamics modeling the mass transfer in space of a fragrance from a fragrance source. The parameters of this computational fluid dynamics model depend on the nature of the fragrance source, whether active or passive, as well as characteristics of mass transfer that can vary depending upon a fragrance source ingredient identifier that can be set within the system. Such models may, for example, show that a particular ingredient presents, at equilibrium conditions, a greater spatial reach than another ingredient.

Such a computational fluid dynamic model may correspond to Menter's Shear Stress Transport turbulence model.

The itinerary definition means 103 is, for example, a computer program executed upon an electronic computing means. This itinerary definition means 103 may, for example, define a route that a user should follow within a space encompassing the volume of fragranced air determined by the fragrance spatial mass transfer calculation means 102.

This route may be determined as a function of the estimated gas phase concentration of an ingredient, or a sum of ingredients, at a particular spatial location. Other parameters may be used in combination or instead, such as the predicted intensity of perception by a user at a particular spatial location.

This route may be shown to the user as a virtual path to be followed in the virtual space corresponding to specific locations in the physical space. Particular points of interest, where the user should interact with the fragrance source, can be marked along that route.

Figure 14:
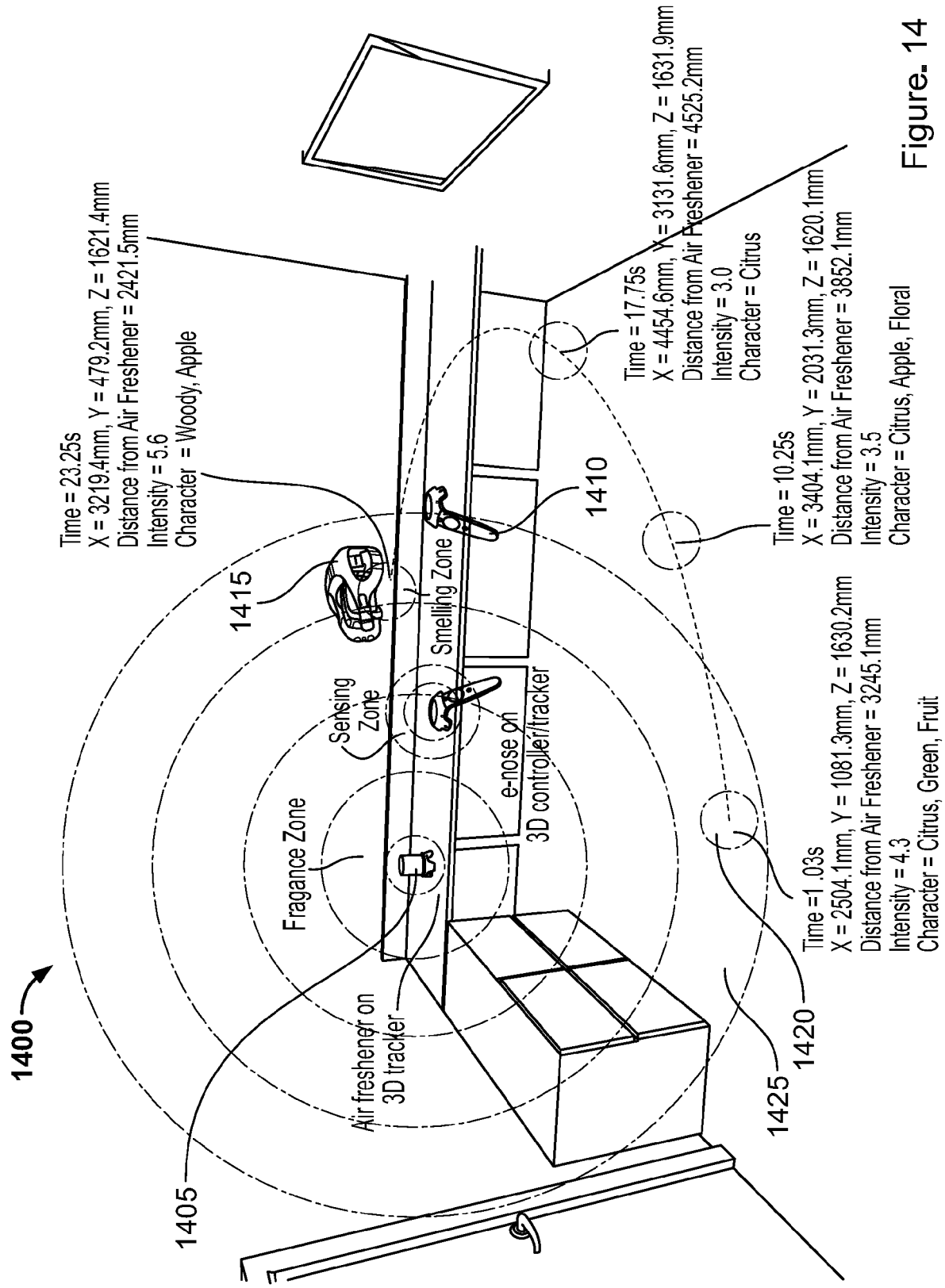
FIG. 14 represents, schematically, a simulation environment of a system object of the present invention.

FIG. 14 shows an example of such a simulation environment 1400. In this environment, which can correspond to a virtual and/or physical environment, a fragrance source 1405 is located. Such a fragrance source 1405 is, for example, an air freshener mounted upon a portable fragrance delivery device which is monitored in its relative position to a facial feature of the user located in the environment 1400. This user is represented by a headset 1415 comprising a display of the virtual environment as well as controllers 1410 to interact with the virtual environment. One of said controllers 1410 may further comprise an electronic nose allowing for the physical measurement of olfactometric properties in a given point in space.

A particular route 1420, determined by the system, is shown with particular locations highlighted and requiring user interaction, such as a measurement or an inhalation of fragranced air. In another example, the user may be asked to describe the tonality of the fragrance at said locations.

In particular embodiments, such as shown in FIG. 1, the system 100 object of the present invention comprises a portable fragrance delivery device activation detection means 104, the relative positioning tracker 110 being activated as a function of said detected activation.

The fragrance delivery device activation detection means 104 is, for example, a switch activated by the activation of the fragrance delivery device 105. Such an activation may correspond to the activation of a spray nozzle, for example. This fragrance delivery device activation detection means 104 allows for the recording, in time and/or space, of the event of activation. This information allows for the trigger of many potential processes, such as the detection of a user behavior as a function of time since activation and/or distance from the point of activation. Another potential process is the modeling of the mass transfer of the fragranced air in space.

Figure 4:
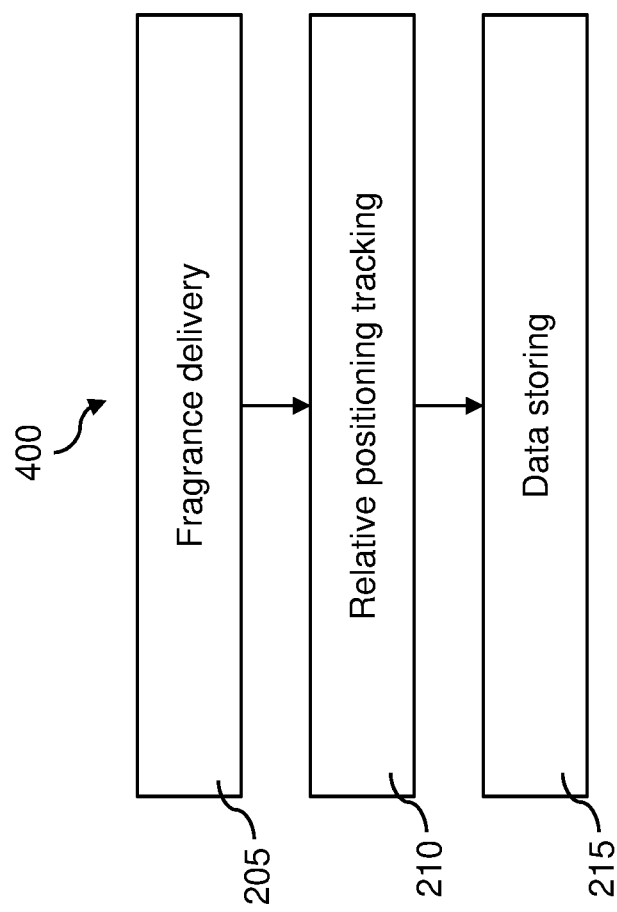
FIG. 4 represents, schematically and in the form of a flowchart, a first embodiment of a method object of the present invention.

FIG. 4 shows a schematic view of a method which is the subject of this invention. This user gesture data collection method 200 comprises:

a fragrance delivery step 205 operated by a portable fragrance delivery device, a relative positioning tracking step 210 to detect the positioning of the portable fragrance device relative a facial feature of a user and a data storing step 215 storing data based on the relative positioning detected.

The fragrance delivery step 205 depends on the nature of the delivery device, such as discussed in relation to FIGS. 1 to 3. For example, the delivery step 205 is achieved, for example, by releasing a fragrant liquid onto a wick.

The relative positioning tracking step 210 corresponds to the operation of the relative positioning tracking means 110 such as discussed in relation to FIGS. 1 to 3.

The data storing step 215 corresponds to the operation of the storing means 115 such as discussed in relation to FIGS. 1 to 3.

The user gesture data collection method 200 can be further improved by additional steps corresponding to the means discussed in relation to FIGS. 1 to 3.

As it is understood, in particular embodiments of this invention, the system object of the present invention can provide a virtual or augmented reality experience that is enhanced by perception of flavor/fragrance, fragranced articles or representative swatches thereof and preserves the fidelity of the original fragrance or the fragranced object to ensure that the fragrance can be evaluated in a simulated real-life experience, a contextual environment or a fictional environment. The accuracy of the fragrance is paramount, including interactions between fragrances and substrates. Non-limiting examples include:
- evaluating fine fragrances on a blotter or fragrance strip similar to a perfumer evaluating fragrance in a laboratory,
- evaluating fine fragrance on artificial skin similar to how a person would perceive fragrance on their own skin,
- evaluating hair swatches to evaluate various shampoos applied to the hair swatch, including the ability to feel the hair swatch on the nose,
- evaluating fabric washed in fragranced laundry detergent, including the ability to feel the fabric on one's nose, simulating someone evaluating a real towel, evaluating the fragrance of a laundry detergent bottle cap, similar to consumer sniffing the cap to get a sense of the fragrance of the detergent contained within the bottle.

The system object of the present invention can provide a virtual reality system that is particularly suited for the perception and experience of multiple fragrances, including fine fragrances, allowing users to rate, try and purchase the fragrance or fragranced article using e-commerce.

The system object of the present invention can provide a system that provides feedback on how the user is interacting with these fragrances. Such a virtual reality system allows for an accurate prediction of the location of the users nose since the headset is already tracked by the system.

FIG. 11, which is not to scale, shows a schematic view of a system which is the subject of this invention. This multisensory experience system 1100 comprises:
- a user gesture data collection system (1101), according to any of the embodiments above, comprising:
  - a passive and portable fragrance delivery device 1105,
  - a delivery device position tracking means 1110,
  - a delivery device position converter 1115 configured to convert the tracked position of the device into a virtual environment position and
  - a digital environment display 1120 comprising a modeling means configured to model, in the digital environment, a virtual image in a position corresponding to the tracked delivery device.

The passive and portable fragrance delivery device 1105 corresponds to the delivery device 105 disclosed with regards to FIGS. 1 to 10 when the delivery means is considered as passive.

The delivery device position tracking means 1110 is, for example, a VR system controller comprising a built-in position tracker. Other variants are described in relation to the relative position tracker 110 of FIGS. 1 to 10.

The delivery device position converter 1115 is, for example, a virtual environment generation software ran by a computing means, said software converting real-life spatial coordinates into virtual space coordinates. This allows to show, in the place of the delivery device position tracked, a virtual image.

The digital environment display 1120 corresponds to the digital environment display 130 disclosed with regards to FIGS. 1 to 10.

In particular embodiments, the system 1100 further comprises:
- a relative positioning tracker 1125 configured to detect the positioning of the portable fragrance device 1105 relative a facial feature of a user and
- a data storing means 1130 storing data based on the relative positioning detected.

The relative positioning tracker 1125 corresponds to the relative positioning tracker 110 disclosed with regards to FIGS. 1 to 10.

The data storing means 1130 corresponds to the data storing means 115 disclosed with regards to FIGS. 1 to 10.

In particular embodiments, the system 1100 further comprises a virtual spatial fragrance zone modeling means 1135 configured to define a virtual volume in proximity of the fragrance delivery device, the relative positioning tracker being configured to detect the positioning of the virtual spatial fragrance zone relative to the tracked facial feature.

The virtual spatial fragrance zone modeling means 1135 corresponds to the virtual spatial fragrance zone modeling means 120 disclosed with regards to FIGS. 1 to 10.

In particular embodiments, the system 1100 further comprises a virtual user smelling zone modeling means 1140 configured to define a virtual volume in proximity of the tracked facial feature, the relative positioning tracker being configured to detect the positioning of the portable fragrance device 1105 or the virtual spatial fragrance zone relative to the virtual user smelling zone.

The virtual spatial smelling zone modeling means 1140 corresponds to the virtual spatial smelling zone modeling means 125 disclosed with regards to FIGS. 1 to 10.

In particular embodiments, the system 1100 further comprises a user gesture detection means 1145, the data stored corresponding at least in part to the detected user gesture.

The user gesture detection means 1145 corresponds to the user gesture detection means 155 disclosed with regards to FIGS. 1 to 10.

In particular embodiments, the user gesture detection means 1145 is configured to detect a gesture corresponding to a smelling event by the user, such event being detected as a function of a distance between the detected positions of the facial feature and the portable fragrance device 1105.

In particular embodiments, the system 1100 further comprises a relative position evolution measurement means 1150 configured to determine, over time, the position of the portable fragrance delivery device 1105 relative to the position of the facial feature, the user gesture detection means 1145 being configured to detect a user gesture based on the relative position evolution measured.

The relative position evolution measurement means 1150 corresponds to the relative position evolution measurement means 160 disclosed with regards to FIGS. 1 to 10.

In particular embodiments, the fragrance delivery device 1105 comprises a fragrance selector 1106 configured to present at least one determined fragrance among a plurality of fragrances.

The fragrance selector 1106 corresponds to the fragrance selector 106 disclosed with regards to FIGS. 1 to 10.

In particular embodiments, the system 1100 further comprises a digital environment event detector 1155 in the digital environment, the selector 1106 being actuated as a function of the digital event detected.

The digital environment event detector 1155 corresponds to the digital environment event detector 145 disclosed with regards to FIGS. 1 to 10.

In particular embodiments, the digital environment display 1120 is configured to be worn on the head of a user, the multisensory system further comprising:
- a spatial position tracking means 1160 being configured to track the position of the digital environment display, a facial position inference means 1165 configured to infer the position of the facial feature based on the digital environment display position tracked.

The spatial position tracking means 1160 corresponds, for example, to the position tracker built-in a VR system headset by design. Other variants are described in relation to the relative position tracker 110 of FIGS. 1 to 10.

The facial position inference means 1165 corresponds to the facial position inference means 140 disclosed with regards to FIGS. 1 to 10.

Figure 13:
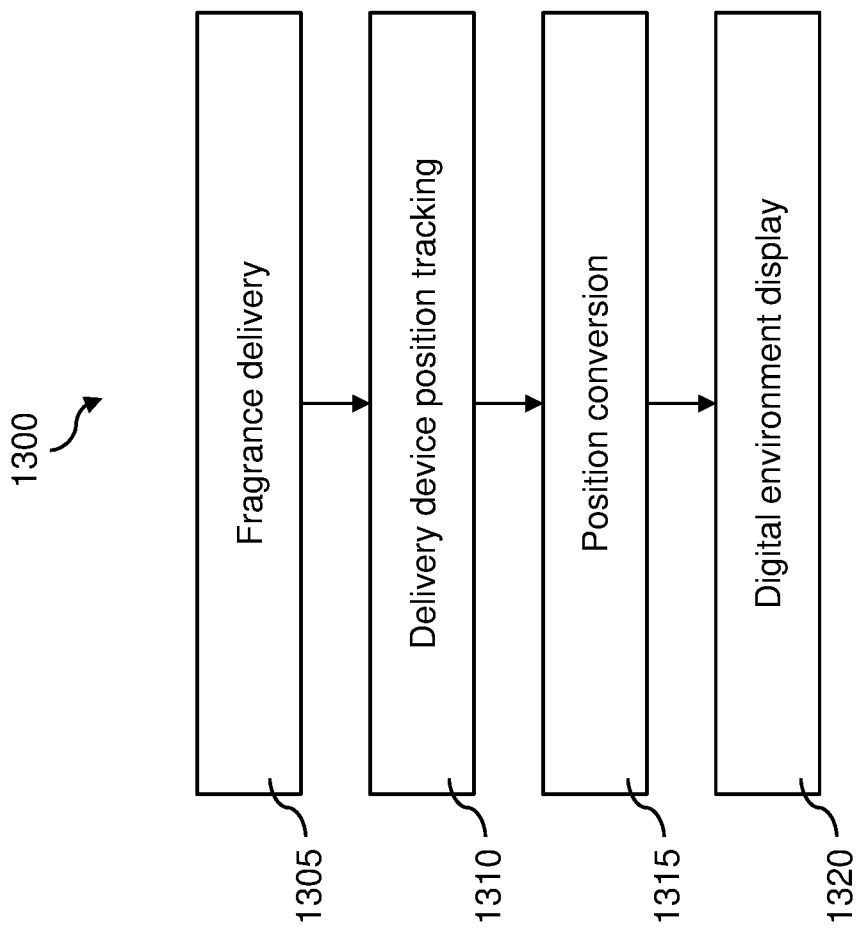
FIG. 13 represents, schematically and in the form of a flowchart, a second embodiment of a method object of the present invention

In particular embodiments, such as shown in FIG. 13, the system 1300 further comprises a robotic arm 1170 configured to hold the portable fragrance delivery device.

The robotic arm 1170 corresponds to the robotic arm 150 disclosed with regards to FIGS. 1 to 10.

In particular embodiments, the portable fragrance delivery device 1105 comprises an artificial human body part 1107 upon which the fragrance is applied.

The artificial human body part 1107 corresponds to the artificial human body part 108 disclosed with regards to FIGS. 1 to 10.

The fragranced item representation 1113 corresponds to the fragranced item representation 113 disclosed with regards to FIGS. 1 to 10.

In particular embodiments, the system 1100 further comprises a user body behavior detection means 1175 or an ambient physical parameter sensor 1180, such body behavior or an ambient physical parameter being stored by the storing means.

The user body behavior detection means 1175 corresponds to the user body behavior detection means 165 disclosed with regards to FIGS. 1 to 10.

In particular embodiments, the system 1100 further comprises a fragrance physical parameter detection means 1185, the fragrance physical parameter detected being stored by the storing means.

The fragrance physical parameter detection means 1185 corresponds to the fragrance physical parameter detection means 175 disclosed with regards to FIGS. 1 to 10.

In particular embodiments, the system 100 further comprises a user input means 112, said user input being stored by the storing means 115. Such user input means 112 can be any human-machine interface traditionally used to collect a user input. For example, such an input means 112 can be a set of keys representative of typical user input such as the keys of a VR controller. In another embodiment, said input means 112 can be a voice command system designed to detect a user's command in a sound signal representative of human speech.

FIG. 13 shows a particular embodiment of the method object of the present invention. This multisensory experience method 1300 comprises:
- a fragrance delivery step 1305 operated by a passive and portable fragrance delivery device,
- a delivery device position tracking step 1310,
- a delivery device position conversion step 1315 to convert the tracked position of the device into a virtual environment position and
- a digital environment display step 1320 comprising a modeling step to model, in the digital environment, a virtual image in a position corresponding to the tracked delivery device.

The fragrance delivery step 1305 operated by a passive and portable fragrance delivery device is achieved by using a fragrance delivery device 1105 such as disclosed in FIGS. 11 and 12.

The delivery device position tracking step 1310 is achieved by using a fragrance delivery device tracking means 1110 such as disclosed in FIGS. 11 and 12.

The delivery device position conversion step 1315 is achieved by using a delivery device converter 1115 such as disclosed in FIGS. 11 and 12.

The digital environment display step 1320 is achieved by using a digital environment display 1120 such as disclosed in FIGS. 11 and 12.

As it is understood, the present system 100 and method 1300 allow for the testing of key performance metrics of fragrances with new and innovative performance evaluation data. Such data can be gesture data by itself of gesture data taken in combination with explicitly stated data by the user. As such, it is therefore possible to create new performance testing protocols including the observation of user gesture as a part of the performance evaluation. The user can be left to freely operate the delivery device or instructed, as part of the protocol, to interact with the device in a given manner.

More advanced testing protocols include the entry of user input relative to a given testing situation. Such user input can be done by voice recognition or by the use of a controller comprising keys—virtual in the case of a touchpad—representative of said input.

The confrontation of explicit and implicit inputs allow for the creation of new performance evaluation metrics or to discard incoherent results.

For example, if a user declares appreciating a fragrance while keeping the delivery device as far as possible from his or her nose, the result can be interpreted as either the likeness of the fragrance is best at arms' length or that the used entered the wrong input. A contextual query can be addressed to the user to solve this ambiguity.

As it is understood, the present invention allows for the creation of new, innovative testing protocols for panelists. For example, FIG. 14 shows a room with a physical table that matches a virtual environment. In this case an air freshener is placed onto the table connected to a 3D tracker. Panelist are asked to walk through the room and evaluate intensity and character of the fragrance over time, while their spatial location of their nose is tracked in real time. Optionally, the panelists carry an electronic nose connected to a tracker or controller to monitor the headspace fragrance concentration. The latter could be a simple VOC detector reporting total VOC concentration or it could be a more advanced e-nose that specifically targets individual fragrance compounds or malodor.

After a prolonged time, the air freshener concentration in the air would reach a steady state, where an established concentration gradient may exist. The closer one gets to the air freshener, the higher the concentration. These concentration gradients may be known from mass transfer simulations (real-time or 'baked') or from measurement using a 3D tracked e-nose mounted to a controller or to the user's headset.

The virtual experience could instruct the user to slowly walk to a position in the room and position the user's nose at a specific location designated with a visual indicator that is hovering in 3D space. The visual indicator may optionally be colored red, until the user gets close enough and may turn green with a chiming sound that the correct location has been reached for evaluation. In this example shown in the illustration, a first visual indicator may represent a concentration in the order of 10-100 ppm of the fragrance. After logging the sensory experience, the user is instructed to move to a second visual indicator which is further away from the source and may represent a concentration of around 0.1-1 ppm. The advantage of this approach is that it uses actual air care products with great fidelity, and presents the user with fragrance at different, but known concentrations in a real-life application.

In another example, a tracker is connected with electrical wires inside the empty aerosol spray to a switch embedded into the spray nozzle of an air freshener. This turns this fragrance dispenser into a fully functional 'game controller' that can be easily integrated in virtual experiences.

This test device can serve as a control for an experiment with an air freshener that contains a fragrance, to see if a person would spray shorter amount of time when the nose smells the fragrance.

In such an example, data on the spatial location of the air freshener is recorded several times per seconds and every record is time stamped down to the millisecond. When the trigger is depressed, a virtual spraying sound is played, and an approximate rendition of a spray pattern using virtual mist/smoke is generated to visualize the fragrance zone. The distance between the fragrance zone (in this case it is the origin of the fragrance source, the nozzle) and the approximate location of the user's nose is recorded as well. From this data one could deduce the average height from which the spray was initiated, with minimum and maximum values indicated as well. Interrupts in the data represent moments where the user was not spraying, allowing for spray counters and spray totalizers to be easily implemented. More preferable would be the implementation of a touch sensitive switch that allows the pressure of application to be measured as well.

This experimental setup can be used for example to test if a user sprays longer or shorter when the concentration of the fragrance is increased. For example, if a stronger fragrance is used, a user is likely to spray shorter since fragrance entering the smelling zone would be detected and would signal to the user that the spray is effective in freshening the air. A weak fragrance could encourage the user to spray more product until sufficient fragrance has entered the smelling zone, signaling that the product is working later.

In particular embodiments, alternative ways to track someone's head and facial features that either can be used with or without VR are considered. Such an example of a head tracking device that could be modified to track the location of the smelling zone is TrackIR (Trademarked) by NaturalPoint (Trademarked).

Other examples of tracking can be considered, such as LiDar devices like the one on an Iphone 12 Pro (Trademarked) or Microsoft Kinect (Trademarked) Xbox360 (Trademarked) and Kinect (Trademarked) for XBOX One (Trademarked) can be used to track facial features.

The invention claimed is:

1. User gesture data collection system, comprising:
   a portable fragrance delivery device,
   a relative positioning tracker configured to detect the positioning of the portable fragrance device relative to a facial feature of a user,
   a controller configured to detect a user gesture made in response to fragrance delivered by the portable fragrance delivery device, said controller is further configured to determine if said gesture corresponds to a smelling event by the user in accordance with a relative distance between the facial feature and the portable fragrance device, and
   a data storing means storing data related to the relative distance and said detected user gesture.

2. User gesture data collection system according to claim 1, wherein said controller is further configured to define a virtual spatial fragrance zone including a virtual volume in proximity of the fragrance delivery device, the relative positioning tracker being configured to detect the positioning of the virtual spatial fragrance zone relative to the tracked facial feature.

3. User gesture data collection system according to claim 1, wherein said controller is further configured to define a virtual user smelling zone including a virtual volume in proximity of the tracked facial feature, the relative positioning tracker being configured to detect the positioning of the portable fragrance device or the virtual spatial fragrance zone relative to the virtual user smelling zone.

4. User gesture data collection system according to claim 3, which comprises a user breathing cycle modeling means, the user smelling zone being defined as a function of the modelled breathing cycle.

5. User gesture data collection system according to claim 1, which further comprises:
   a digital environment display configured to be worn on the head of the user,
   a spatial position tracker being configured to track the position of the digital environment display,
   wherein said controller is further configured to infer the position of the facial feature based on the digital environment display position tracked.

6. User gesture data collection system according to claim 1, in which the portable fragrance delivery device comprises a fragrance selector configured to present at least one determined fragrance among a plurality of fragrances.

7. User gesture data collection system according to claim 6, which further comprises a digital environment event detector, the selector being actuated as a function of the digital event detected.

8. User gesture data collection system according to claim 1, in which the portable fragrance delivery device comprises a passive fragrance delivery means.

9. User gesture data collection system according to claim 1, which further comprises a robotic arm configured to hold the portable fragrance delivery device.

10. User gesture data collection system according to claim 1, in which the portable fragrance delivery device comprises an artificial human body part or a fragranced item representation upon which the fragrance is applied.

11. User gesture data collection system according to claim 1, wherein said controller is configured to determine, over time, the position of the portable fragrance delivery device relative to the position of the facial feature, the controller is further configured to detect a user gesture based on the relative position evolution measured.

12. User gesture data collection system according to claim 1, which further comprises a fragrance physical parameter detection means, the fragrance physical parameter detected being stored by the storing means.

13. User gesture data collection system according to claim 1, which further comprises a user input means, said user input being stored by the storing means.

14. User gesture data collection system according to claim 1, wherein said controller is configured to determine a route to be followed by an operator as a function of the spatial mass transfer calculated, the relative position tracker being configured to operate in different locations of the route defined.

15. User gesture data collection system according to claim 1, which further comprises a portable fragrance delivery device activation detection means, the relative positioning tracker being activated as a function of said detected activation.

16. Multisensory experience system, comprising:
- a user gesture data collection system, according to claim 1, comprising:
  - a passive and portable fragrance delivery device,
  - a delivery device relative position tracking means,
  - wherein the controller configured to convert the tracked relative position of the device into a virtual environment position said controller is further configured to characterize the user's behavior relative to the fragrance based on the tracked relative position and
- a digital environment display comprising a modeling circuit configured to model, in the digital environment, a virtual image in a position corresponding to the tracked delivery device.

17. Multisensory experience system according to claim 16, further comprising:
- a relative positioning tracker configured to detect the positioning of the portable fragrance device relative a facial feature of a user and
- a data storing means storing data based on the relative positioning detected.

18. Multisensory experience system according to claim 16, which further comprises a user body behavior detection means or an ambient physical parameter sensor, such body behavior or an ambient physical parameter being stored by the storing means.

19. Multisensory experience system according to claim 16, which further comprises a fragrance physical parameter detection means, the fragrance physical parameter detected being stored by the storing means.

20. Multisensory experience system according to claim 16, wherein said controller is further configured to define a virtual spatial fragrance zone including a virtual volume in proximity of the fragrance delivery device, the relative positioning tracker being configured to detect the positioning of the virtual spatial fragrance zone relative to the tracked facial feature.

21. Multisensory experience system according to claim 16, wherein said controller is further configured to define a virtual user smelling zone including a virtual volume in proximity of the tracked facial feature, the relative positioning tracker being configured to detect the positioning of the portable fragrance device or the virtual spatial fragrance zone relative to the virtual user smelling zone.

22. Multisensory experience system according to claim 16, wherein said controller is configured to determine, over time, the position of the portable fragrance delivery device relative to the position of the facial feature, the controller is further configured to detect a user gesture based on the relative position evolution measured.

23. Multisensory experience system according to claim 16, in which the fragrance delivery device comprises a fragrance selector configured to present at least one determined fragrance among a plurality of fragrances.

24. Multisensory experience system according to claim 23, which further comprises a digital environment event detector in the digital environment, the selector being actuated as a function of the digital event detected.

25. Multisensory experience system according to claim 16, in which the digital environment display is configured to be worn on the head of a user, the multisensory system further comprising:
- a spatial position tracker being configured to track the position of the digital environment display,
- wherein said controller is further configured to infer the position of the facial feature based on the digital environment display position tracked.

26. Multisensory experience system according to claim 16, in which the fragrance delivery device comprises several fragrance sources, at least two said sources being separated by a shield.

27. Multisensory experience system according to claim 16, in which the fragrance delivery device comprises several fragrance sources, at least two said sources are organized along a rotation axis, the system further comprising a rotating housing comprising a slit configured to selectively overlap with at least one fragrance source depending on the rotation angle of the said housing.

28. User gesture data collection method, comprising:
- a fragrance delivery step operated by a portable fragrance delivery device,
- a relative positioning tracking step to detect the positioning of the portable fragrance device relative a facial feature of a user
- detecting a user gesture made in response to fragrance delivered by the portable fragrance delivery device and determining if said gesture corresponds to a smelling event by the user in accordance with a relative distance between the facial feature and the portable fragrance device, and
- storing data related to the relative distance and said detected user gesture.

29. Multisensory experience method, which comprises:
- a fragrance delivery step operated by a passive and portable fragrance delivery device,
- a delivery device relative position tracking step,
- a delivery device relative position conversion step to convert the tracked relative position of the device into a virtual environment position,
- a modelling step characterizing the user's behavior in response to the fragrance delivered based on the tracked relative position, including detecting a user gesture made in response to fragrance delivered by the portable fragrance delivery device and determining if said gesture corresponds to a smelling event by the user in accordance with a relative distance between the facial feature and the portable fragrance device, and
- a digital environment display step comprising a modeling step to model, in the digital environment, a virtual image in a position corresponding to the tracked delivery device.

* * * * *